(12) United States Patent
Etkin et al.

(10) Patent No.: US 6,837,106 B2
(45) Date of Patent: Jan. 4, 2005

(54) GRAVITY GRADIOMETRY

(75) Inventors: Bernard Etkin, North York (CA); John Barry French, Oakville (CA); Bjarni V. Tryggvason, Boca Raton, FL (US); Frank J. van Kann, Nedlands (AU)

(73) Assignee: Business Arts Inc., Mississauga (CA)

( * ) Notice: Subject to any disclaimer, the term of this patent is extended or adjusted under 35 U.S.C. 154(b) by 0 days.

(21) Appl. No.: 09/995,336

(22) Filed: Nov. 27, 2001

(65) Prior Publication Data

US 2002/0092350 A1 Jul. 18, 2002

Related U.S. Application Data

(60) Provisional application No. 60/253,538, filed on Nov. 28, 2000.

(51) Int. Cl.[7] ................................................. G01N 7/16
(52) U.S. Cl. ..................................................... 73/382 G
(58) Field of Search .......................... 73/382 G, 382 R; 702/2; 248/550

(56) References Cited

U.S. PATENT DOCUMENTS

| | | | |
|---|---|---|---|
| 3,062,051 A | 11/1962 | Slater et al. | |
| 3,474,672 A | 10/1969 | LaCoste et al. | |
| 3,564,921 A | 2/1971 | Bell | |
| 3,630,086 A | 12/1971 | Wilk | |
| 3,633,003 A | 1/1972 | Talwani | |
| 3,731,537 A | 5/1973 | Trageser | |
| 4,399,694 A * | 8/1983 | Mayer ...................... | 73/382 G |
| 4,435,981 A | 3/1984 | Carson et al. | |
| 5,341,681 A | 8/1994 | Molny et al. | |
| 5,357,802 A | 10/1994 | Hofmeyer et al. | |
| 5,505,555 A | 4/1996 | Van Kann et al. | |
| 5,587,526 A | 12/1996 | Lumley et al. | |
| 5,661,649 A | 8/1997 | Carson et al. | |
| 5,668,315 A | 9/1997 | Van Kann et al. | |
| 5,734,104 A | 3/1998 | Panenka | |
| 5,804,722 A | 9/1998 | Van Kann et al. | |
| 5,817,939 A | 10/1998 | Lumley et al. | |
| 5,892,151 A | 4/1999 | Niebauer et al. | |
| 5,922,951 A | 7/1999 | O'Keefe et al. | |
| 5,962,782 A | 10/1999 | O'Keefe et al. | |
| 6,196,514 B1 * | 3/2001 | Kienholz ................... | 248/550 |
| 6,212,952 B1 | 4/2001 | Schweitzer et al. | |
| 6,501,203 B2 * | 12/2002 | Tryggvason ............... | 248/550 |

FOREIGN PATENT DOCUMENTS

WO     WO 9505576     2/1995

OTHER PUBLICATIONS

Swain, Christopher J. "Horizontal acceleration corrections in airborne gravimetry" Geophysics, Society of Exploration Geophysicists, Tulsa, US, vol. 6, No. 1, Jan.–Feb. 1996, pp. 273–276.

(List continued on next page.)

Primary Examiner—John E. Chapman
(74) Attorney, Agent, or Firm—George A. Seaby

(57) ABSTRACT

A gravity gradiometer is combined with a two-stage actively controlled isolation system. The gravity gradiometer and two stage isolation system may then be mounted within (or on) a mobile vehicle such as, for example, an aircraft. It has been recognized by the inventors herein that the accelerations imparted to an aircraft during normal operations can be separated through system design into two relatively distinct regimes within the frequency domain. The invention provides a first isolation mount, which forms part of the isolation system, to isolate accelerations (and resulting translations) falling within a first of the two frequency regimes. The second isolation mount, which is mounted to the first isolation mount, isolates accelerations falling within the second of the two frequency regimes. A gravity gradiometer can then be mounted to the second isolation mount. As a result of housing the gravity gradiometer within the nested isolation system (a combination of the first and second isolation mounts), the gravity gradiometer is substantially isolated from the accelerations experienced by the mobile vehicle. Consequently, gravity gradients measured by the gravity gradiometer are relatively noise free and provide heretofore-unobtainable accuracy.

14 Claims, 17 Drawing Sheets

OTHER PUBLICATIONS

Tryggvason, Bjarni et al. "Acceleration Levels and Operation of the Microgravity Vibration Isolation Mount (MIM) on the Shuttle and the MIR Space Station", AIAA–99–0578, American Institute of Aeronautics and Astronautics, 1998, pp 1–12.

Stewart, William Y. et al. "Microgravity Vibration Isolation Mount,an Example of a Multi–Processor Architecture in a Space Application,"Canadian Space Agency: International Conference on Signal Processing Applications & Technology, Sep. 1998.

Kienholz, David A. "Active Alignment and Vibration Control System for Large Airborne Optical System", SPIE: Smart Structures and Materials Conference, Mar. 2000.

Tryggvason, Bjarni et al. "The Canadian Space Agency's Vibration Isolation Facilities Development for the International Space Station", 52$^{nd}$ International Astronautical Congress (France), IAF–01–J.5.03, Oct. 2001.

Kleusberg, Alfred et al. "Airborne Gravimetry and the Global Positioning System" 1990's—Decade of Excellence in the Navigation Sciences, Las Vegas, Mar. 20–23, 1990, Proceedings of the Position Location and Navigation Symposium (PLANS), New York, IEEE, US, Mar. 20, 1990, pp. 273–278.

AIAA, *Development and Performance of a Three Degree of Freedom Large Motion Vibration Isolation Mount for the KCC–135 Aircraft*, by B.V. Tryggvason, B.Y. Stewart and E. A. Sloot; 31st Aerospace Sciences Meeting & Exhibit, Jan. 11–14, 1993/Reno, NV, 12 pages.

* cited by examiner

GRAVITY GRADIOMETRY

FIELD OF THE INVENTION

The present invention relates to an apparatus, method and system for measuring gravitational acceleration and the gradient in the gravitational acceleration (termed the gravity gradient) and, in particular, to an apparatus, method and system for the exploration and measurement of the local variations in the gravitational field of bodies such as the earth.

BACKGROUND TO THE INVENTION

The strength of a local gravitational field depends upon the proximity to the mass of an object(s). The mass of an object, in turn, is dependent upon the density of the material of the object and the volume of the object. Accordingly, density variations of geological structures such as mineral deposits, oil reservoirs, underground tunnels or caverns have specific gravity signatures. These signatures, if measured with sufficient accuracy, can be used to assist in the identification of the corresponding geological structures.

Accordingly, although for most purposes the gravitational acceleration at the surface of the earth appears relatively constant, the gravitational acceleration does in fact change from place to place. These changes in the gravitational acceleration result from variations in the density of the material of the earth (or other celestial bodies such as an asteroid, moon or the like). For example, a measurement of the gravitational acceleration taken above a network of large underground caves (i.e., areas of relatively little mass) will be less than a similar measurement taken above a large dense deposit of nickel.

Compared to the Earth's gravitational acceleration at the surface, the variations in the gravitational acceleration are quite small. The nominal gravitational acceleration at the earth's surface resulting primarily from the Earth's mass is 9.81 meters per second per second ($m/s^2$). A unit often used for acceleration is 1 g, which is defined as 9.81 $m/s^2$. Variations in the gravitational acceleration are often measured in milligals (mgals) which is defined as $10^{-5}$ $m/s^2$, and which is approximately equal to one-millionth of 1 g. The gravity gradient, which is defined as the rate of change of gravitational acceleration with respect to distance, has the units of $m/s^2/m$ (or $1/s^2$). For convenience, a defined unit for gravity gradient is the Eotvos, where one Eotvos (Eö) is defined to be equal to $10^{-9}$ $m/s^2/m$, i.e., $10^{-9}/s^2$, or $10^{-4}$ mgals/meter.

The gravitational acceleration due to an object decreases as the inverse of the square of the distance from the object (i.e., as the distance from the object doubles, the gravitational acceleration due to the object decreases by a factor of four) and it increases in direct proportion to the mass of the object. The direction of the gravitational acceleration depends on the distribution of mass within the object. Far from the object the gravitational acceleration is directed towards the center of mass of the object. However, close to the surface of the object, the strength and direction of the gravitational acceleration depends on the detailed distribution of the mass variation near the surface of the object. For example, near the surface of the earth, the gravitational acceleration due to the Earth will vary according to the mass distribution near the surface. Near, for example, the bottom of a mountain, the gravitational acceleration will have a small component directed horizontally towards the mountain, as well as the larger component directed vertically towards the center of the Earth. Near the top of the mountain the horizontal component would be greatly reduced. In three-dimensional space, the gravitational acceleration can be expressed as a vector having three elements (one for each direction): $g_x$, $g_y$, and $g_z$. The magnitude of these three components, and hence the magnitude and direction of the overall gravitational acceleration will thus vary spatially according to the detailed distribution of the mass within the gravitating object. The gravity gradient (G) is a measure of the rate of change of the gravitational acceleration with respect to distance. So, for example, as the gravitational acceleration is measured at different locations, the values of the components $g_x$, $g_y$, and $g_z$ will vary. In general each of these three gravitational acceleration components will vary with each of the three spatial coordinates. This leads to a nine component tensor for the gravity gradient, G. The components of the gravity gradient tensor are distinguished symbolically according to which gravitational acceleration component is being considered and which spatial direction is being considered. Thus the symbol $G_{xz}$ is used to identify the rate of change of the $g_x$ acceleration component with changes in the vertical direction (z). As an example, if the gravitational acceleration component, $g_x$, is measured along a line running vertically from the bottom of a valley, and the mountain narrows from its base to its peak, the gravitational field measured in the x-direction will decrease. The rate of change of $g_x$ with vertical distance is represented by $G_{xz}$. The gravitational component in the x-direction will also change along a horizontal line (i.e., constant z) becoming larger closer to a mountain. This gravity gradient component is represented by the symbol $G_{xx}$. Finally, the gravitational acceleration in the x-direction will in general vary along a horizontal line in the y-direction. This gravity gradient component will be represented by $G_{xy}$. Similarly, changes in the gravitational acceleration for the remaining two components ($g_y$ and $g_z$) as measurements are taken in each of the three directions will be represented by $G_{yx}$, $G_{yy}$, $G_{yz}$, $G_{zx}$, $G_{zy}$ and $G_{zz}$, respectively. The combination of these nine gravity gradient components form what is known as the gravity gradient tensor.

$G_{zz}$, the vertical gravity gradient at the Earth's surface, is about 3000 Eö, i.e., $3 \times 10^{-6}$ $m/s^2/m$, whereas perturbations in $G_{zz}$ due to mineral deposits can be in the range of 1 Eö to 100 Eö.

It is a fundamental law of physics that, at an infinitesimal point, acceleration due to gravity is indistinguishable from acceleration due to other causes. That is, any device capable of detecting the acceleration due to gravity will also respond to acceleration due to other causes. Because of this, currently available devices capable of sensing acceleration with sufficient resolution and accuracy to detect the variations in the gravitational acceleration due to geological structures are typically land-based stationary instruments, as opposed to instruments mounted in a moving craft or vehicle. This is required because of the above described difficulty in distinguishing variations in gravitational acceleration caused by geological structures from the acceleration of the moving craft or vehicle in which the device is carried.

A gravimeter is a device sometimes used in geological surveying to measure the Earth's gravitational acceleration. By repeating the measurements at many locations a map of the gravitational acceleration can be obtained, which can then be used to locate geological features. A simple gravimeter is essentially an accelerometer (a device for measuring accelerations) such as a mass supported on a spring and constrained to move in only one direction, e.g., aligned in the vertical or z-direction along the axis of the spring. An acceleration along this z-axis causes the spring to deflect. The deflection can be detected to produce an output proportional to the acceleration in the z-direction less the acceleration due to gravity in the same axis (i.e., an output of $a_z - g_z$).

As described above, the variation in the gravitational acceleration due to an anomaly is very small in comparison to the background gravitational acceleration and also often small in comparison to the acceleration of the vehicle. Since a gravimeter cannot distinguish between accelerations of a moving vehicle and changes in gravitational acceleration (which can be several orders of magnitude smaller), accurate measurements of the variation in the gravitational acceleration through use of an instrument in a mobile vehicle is extremely difficult. Attempts to remove the vehicle component of the measured acceleration, (e.g., through use of the global positioning system (GPS), to generate an approximation of the accelerations of the vehicle), have produced improvements but have not led to systems with a high enough resolution for effective airborne exploration, particularly for mineral deposits.

It is well recognized that an alternative to directly measuring gravitational acceleration from a mobile vehicle is to directly measure one or more components of the gravity gradient tensor, referenced above. Measuring the gravity gradient components can have considerable advantages.

It has been noted that while variations in the gravitational acceleration caused by a density anomaly may be small in comparison to the background gravitational acceleration, the relative perturbation in the gravity gradient created by a density anomaly near the surface relative to typical gravity gradients at the Earth's surface can be much larger. The local gravitational acceleration (which depends on the mass of an object and the proximity to that mass) falls off with the square of the distance to that mass (Newton's law of gravitation), whereas the gravity gradient (which is a spatial derivative) falls off with the cube of the distance from the mass. As a result, it has been shown that measuring the gravity gradient directly has advantages for locating geological features that lie within a few kilometers of the Earth's surface.

Referencing FIG. 9, a simple gravity gradiometer 1300 (a device for measuring a gravity gradient) is a balance beam 1302 with equal masses on either side of a pivot point 1304 and a torsion spring resisting rotation. If there is no gravity gradient (i.e., the gravitational acceleration is uniform), the gravitational forces on the masses would be equal on both sides of the pivot point and there would be no rotation of the beam. However, in a non-uniform gravity field, the balance beam, if not vertical, will rotate about the pivot 1304 with the one side of the beam being influenced by a stronger gravitational force $m(g_0 + \Delta g)$ and the other side of the beam being influenced by a relatively lesser gravitational force $m(g_0)$. The amount of deflection (which is likely very small) is proportional to the difference (i.e., to the gravity gradient multiplied by the moment arm), and is inversely proportional to the rotational stiffness of the pivot. A translational acceleration of the pivot, and hence the balance beam, will cause no rotation. Therein lies a principal advantage of the gravity gradiometer.

An important improvement on the single beam gravity gradiometer is the two-beam "crossed dumbbell" gravity gradiometer. In such a gravity gradiometer, the dumbbells could be simple rectangular bars (FIG. 6).

Under the influence of the nominal vertical gravity gradient $G_{zz}$ near the Earth's surface, the dumbbells will scissor (i.e., rotate in opposite directions) to an equilibrium position. If the instrument is moved to a location above an excess mass causing a greater $G_{zz}$, the bars will close slightly to a new equilibrium position.

However, almost all gravity gradiometers, including the dumbbell type of gravity gradiometer, when mounted in a moving vehicle will experience some disturbances as a result of displacement of the vehicle from a desired path and internal vibrations of the components of the vehicle. These disturbances can cause the sensor components to vibrate, generating random and potentially large rotations of the beams, making it difficult to resolve the beam rotations due to the gravity gradient.

A system that additionally addresses the problems of vehicle displacement from its ideal path and vibrations as noted above is desired. Current analysis indicates that such a system will provide improved measurement of the gravity gradients over current systems and will be of significant advantage in operation, particularly for geophysical exploration.

SUMMARY OF THE INVENTION

According to the present invention, a gravity gradiometer is combined with a two-stage actively controlled motion isolation system. The gravity gradiometer and two stage isolation system may then be mounted within (or on) a mobile vehicle such as, for example, an aircraft.

Although a specific type of gravity gradiometer, which is described in some detail in this disclosure, is a component of the preferred embodiment, the invention can be formed using other types of gravity gradiometers.

The vehicle disturbances can be quantified by measuring the attendant accelerations, whether those associated with displacements of the vehicle from its ideal path or those associated with internal vibrations of the vehicle components. It has been recognised by the inventors herein that the accelerations imparted to an aircraft or other mobile vehicle during normal operations can, through the system design, be separated into relatively distinct regimes within the frequency domain. The invention provides for an actively controlled isolation system between the vehicle and the gravity gradiometer that can be tailored according to frequency regime and different gravity gradiometer response characteristics, and to different environments (cabin restrictions and vehicle accelerations will be specific to different vehicles). The invention provides for a two-stage (coarse and fine stage) isolation system that effectively separates accelerations into two frequency regimes. The first isolation stage or mount attenuates accelerations (and resulting translations) particularly those of low frequency. This stage provides relatively large displacement movements of the gravity gradiometer relative to the aircraft structure through operation of a Coarse Isolation Mount (CIM). The CIM limits the relative displacement with a weak restoring force such that the probability of a payload (e.g., a gravity gradiometer) reaching the physical limits of the system (i.e., the vehicle cabin) in normal operation is small. The CIM will have its own dynamics and will inevitably introduce some higher frequency disturbances. The second isolation stage is mounted to (or nested within) the first isolation stage, and reduces linear accelerations in all three axis, particularly of high frequency, including some which can be transmitted through and amplified by the CIM dynamics. This second isolation stage also provides rotational isolation about all three axis.

The gravity gradiometer or gravity gradiometer system (a dewar containing the gravity gradiometer in the case of cryogenic gravity gradiometers) is mounted to the second isolation mount. As a result of the gravity gradiometer being nested within the isolation system (a combination of the first and second isolation mounts), the gravity gradiometer is substantially isolated from the accelerations experienced by the mobile vehicle.

The specific performance characteristics of the isolation system, comprising the first and second isolation mounts, are tailored having regard to: (1) the specific atmospheric conditions, and the characteristics of the vehicle or craft in such atmospheric conditions, and (2) the specific characteristics of the gravity gradiometer.

The result of this system is that gravity gradient signals measured by the gravity gradiometer are relatively free of noise produced by translational as well as rotational vehicle accelerations, and provide previously unobtainable resolution and accuracy.

In one aspect of the invention, there is provided a gravity gradient measuring system for mounting in a vehicle. The gravity gradient measuring system includes a coarse stage isolation mount adapted to attenuate, above a first low pass cutoff frequency, displacements imparted on the gravity gradient measuring system, a fine stage isolation mount adapted to attenuate, above a second low pass cutoff frequency, vibrations imparted on the gravity gradient measuring system, where the vibrations are characterized by a minimum frequency, where the second low pass cutoff frequency is greater than the first low pass cutoff frequency and less than the minimum frequency of the vibrations, the fine stage isolation mount mounted to the coarse stage isolation mount and a gravity gradiometer mounted to the fine stage isolation mount.

In a further aspect of the invention there is provided an isolation system for facilitating measurement of a gravity gradient in a moving vehicle. The isolation system includes a coarse stage isolation mount adapted to attenuate, above a first low pass cutoff frequency, displacements, the coarse stage isolation mount including a support platform, a fine isolation mount adapted to attenuate, above a second low pass cutoff frequency, vibrations that are characterized by a minimum frequency, where the second low pass cutoff frequency is greater than the first low pass cutoff frequency and less than the minimum frequency of the vibrations, the fine stage isolation mount including a base mounted to the support platform and a component whose position relative to the base is variable and where a gravity gradiometer can be mounted to the component of the fine stage isolation mount.

In a further aspect of the invention there is provided an apparatus for measuring gravity gradients. The apparatus includes a means for isolating, above a first low pass cutoff frequency, displacements, a means for isolating, above a second low pass cutoff frequency, vibrations, where the vibrations are characterized by a minimum frequency, where the second low pass cutoff frequency is greater than the first low pass cutoff frequency and less than the minimum frequency of the vibrations, a gravity gradiometer mounted to the means for isolating vibrations and where the means for isolating vibrations is mounted to the means for isolating displacements.

In a further aspect of the invention there is provided a method for obtaining fine resolution gravity gradient data. The method includes transporting a gravity gradiometer in a mobile vehicle, the mobile vehicle experiencing accelerations and displacements, in a coarse isolating stage, isolating, above a first low pass cutoff frequency, the accelerations and displacements, in a fine isolation stage, isolating, above a second low pass cutoff frequency, the accelerations and displacements, where the accelerations and displacements are characterized by a minimum frequency, where the second low pass cutoff frequency is greater than the first low pass cutoff frequency and less than the minimum frequency of the vibrations, tracking a position of the mobile vehicle in the six degrees of freedom associated with motion of a rigid body, during isolating the accelerations and displacements in the coarse and fine stages, measuring gravity gradients using a gravity gradiometer and tabulating the gravity gradients as a function of the position of the mobile vehicle.

In a further aspect of the invention there is provided a gravity gradient map of a body, where the map is generated by a general purpose computer adapted to receive gravity gradient signals from a gravity gradiometer mounted to a fine motion isolation mount, the fine motion isolation mount mounted to a coarse motion isolation mount, the coarse motion isolation mount housed within a vehicle, receive position signals tracking the position of the vehicle relative to the Earth and tabulate the gravity gradient signals as a function of the position signals so as to generate a gravity gradient map of a portion of the Earth.

In a further aspect of the invention there is provided a computer readable media containing data representative of gradient gradients, the data generated by: transporting a gravity gradiometer in a mobile vehicle, the mobile vehicle experiencing accelerations and displacements, in a coarse stage, attenuating, above a first low pass cutoff frequency, the accelerations and displacements, in a fine stage, attenuating, above a second low pass cutoff frequency, the accelerations and displacements, where the accelerations and displacements are characterized by a minimum frequency, where the second low pass cutoff frequency is greater than the first low pass cutoff frequency and less than the minimum frequency of the vibrations and, during the attenuating in the coarse and fine stages, measuring gravity gradients using a gravity gradiometer.

In a further aspect of the invention there is provided an aircraft adapted to generate data corresponding to gravity gradient measurements. The aircraft includes a coarse stage isolation mount adapted to attenuate, above a first low pass cutoff frequency, displacements, the coarse stage isolation mount mounted within the aircraft, a fine stage mount adapted to attenuate, above a second low pass cutoff frequency, vibrations, where the vibrations are characterized by a minimum frequency, where the second low pass cutoff frequency is greater than the first low pass cutoff frequency and less than the minimum frequency of the vibrations, the fine stage isolation mount mounted to the coarse stage isolation mount and a gravity gradiometer mounted to the fine stage isolation mount.

In a further aspect of the invention there is provided a body causing a gravity gradient, the body identified by transporting a gravity gradiometer in a mobile vehicle, the mobile vehicle experiencing accelerations and displacements relative to a straight, level, constant velocity path relative to the body, in a coarse isolation stage, isolating, above a first low pass cutoff frequency, the accelerations and displacements, in a fine isolating stage, isolating, above a second low pass cutoff frequency, the accelerations and displacements, where the accelerations and displacements are characterized by a minimum frequency, where the second low pass cutoff frequency is greater than the first low pass cutoff frequency and less than the minimum frequency of the vibrations, tracking a position of the mobile vehicle, during the isolating in the coarse and fine stages, measuring gravity gradients using a gravity gradiometer and tabulating the gravity gradients as a function of the position of the mobile vehicle.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

In figures which illustrate, by way of example only, embodiments of the present invention.

DETAILED DESCRIPTION OF THE PREFERRED EMBODIMENTS

Figure 7:
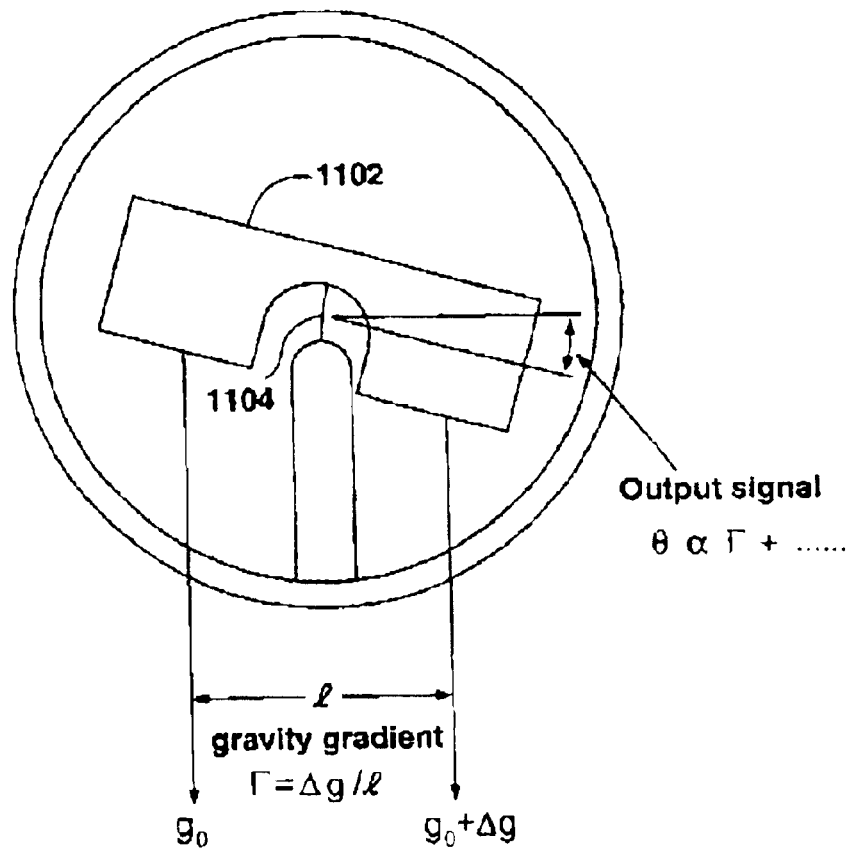
FIG. 7 is a stylised representation of how a gravity gradient produces a signal in a simple balance beam gravity gradiometer.

Referencing FIG. 7, the inventors have noted that, ideally, the center of mass of each dumbbell 1102 in a crossed dumbbell gravity gradiometer will be exactly coincident with its center of rotation. This rotation occurs about a pivot, which can conveniently be in the form of a web connecting the dumbbell to the instrument body. In this case the web also acts as a torsion spring. Such a structure is described in U.S. Pat. Nos. 5,804,722, 5,505,555 and 5,668,315 issued to Van Kann.

The elegance of this concept lies in its ability, at least ideally, to discriminate against translational and angular accelerations. With the center-of-mass of each bar 1102 coincident with its center of rotation, except for second order effects described below, no net torques are produced by translational accelerations, so no scissoring rotations occur due to translational accelerations.

Figure 8:
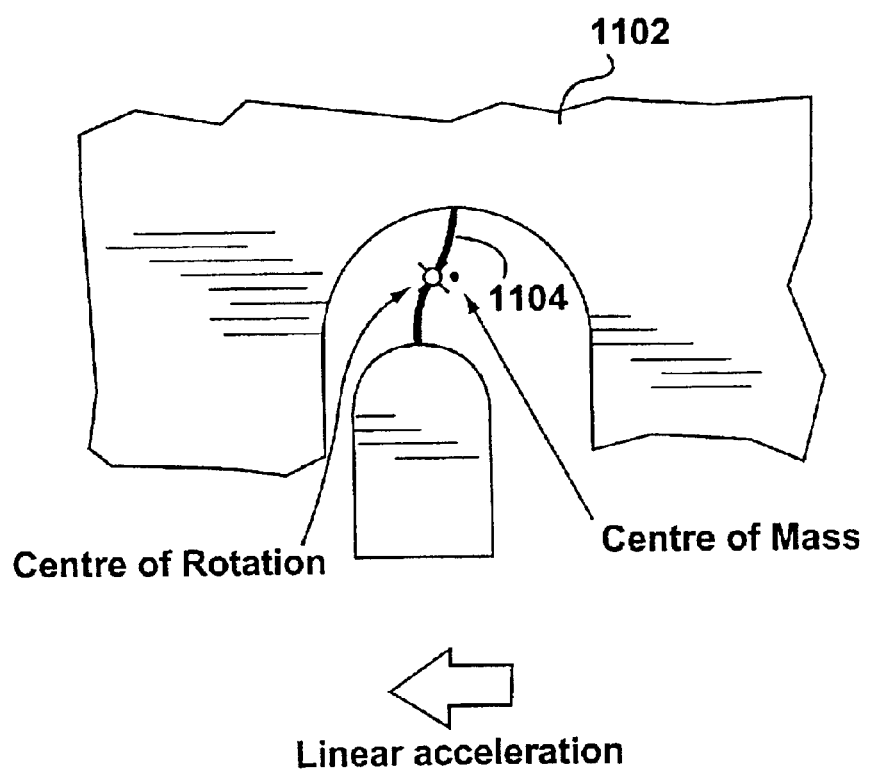
FIG. 8 is a graphical representation of the distortion of the elastic web pivot created by translational accelerations.
Figure 9:
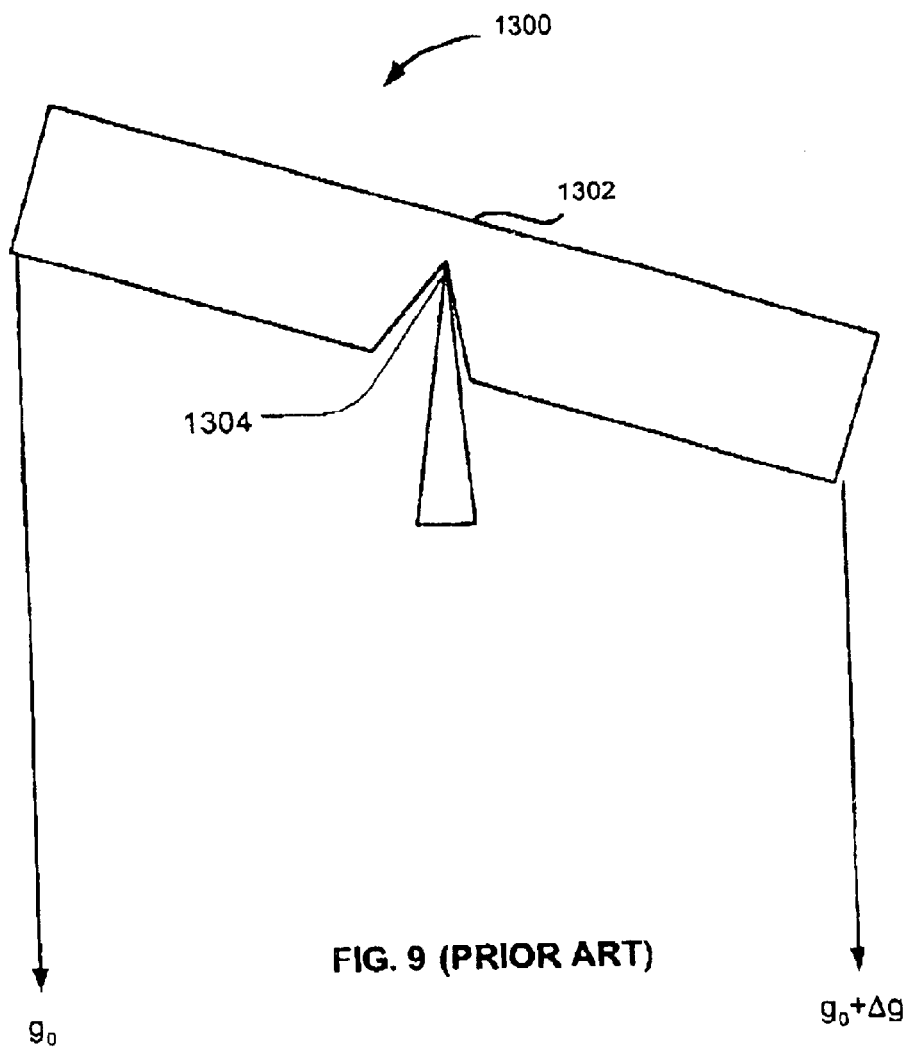
FIG. 9 is a stylised graphical representation of a balance beam gradiometer.

For the effect of translational accelerations, it has been noted by the inventors that all real instruments depart from the ideal, in that the center of mass can never be exactly coincident with the center of rotation (see FIG. 8), and also the elastic web 1104 does not act as a perfect pivot. Therefore, translational accelerations cause two unwanted effects: a rotation of each bar which is directly proportional to the distance between the center of mass and the axis of rotation of the bar; and a second order effect caused by a distortion of the elastic web pivot (1104—FIG. 8) from a planar element into an "S" shaped element (FIG. 8). The S-shaped bend in the elastic web induces a separation between the center of mass and the center of rotation. This separation couples with the translational acceleration to cause a rotation of each bar. Thus it is necessary to provide excellent isolation from translational accelerations.

During angular acceleration, if the dumbbells and their torsion mounts are perfectly matched, each dumbbell experiences the same relative rotation in the same direction and so no scissoring occurs. However, in a real, as distinct from an ideal gradiometer, the torsion characteristics of the two dumbbells can never be perfectly matched. In addition, although angular acceleration (e.g., a roll, pitch or yaw in an aircraft) will in general cause both dumbbells to rotate with respect to their housing, this could close the small gap between the dumbbells and the housing and prevent the instrument from sensing the gravity gradient. Thus, it is necessary to provide excellent isolation from rotational accelerations.

In general the isolation system must provide isolation in all three linear degrees of freedom (DOF) and all three rotational DOFs, i.e., a six DOF isolation system is required. Specific configurations may reduce the sensitivity to accelerations in some DOFs, as discussed further below. In the following, the three linear and three rotational DOFs will in general be referred to as the six rigid body position DOFs.

While the above describes the responses of the "crossed dumbbell" gravity gradiometer to translational motion, it is believed that all forms of gravity gradiometers will have some level of unwanted response to translational acceleration. The invention described herein, in part, provides a system, apparatus and method which addresses, to a degree, these unwanted responses to all types of acceleration including.

Figure 1:
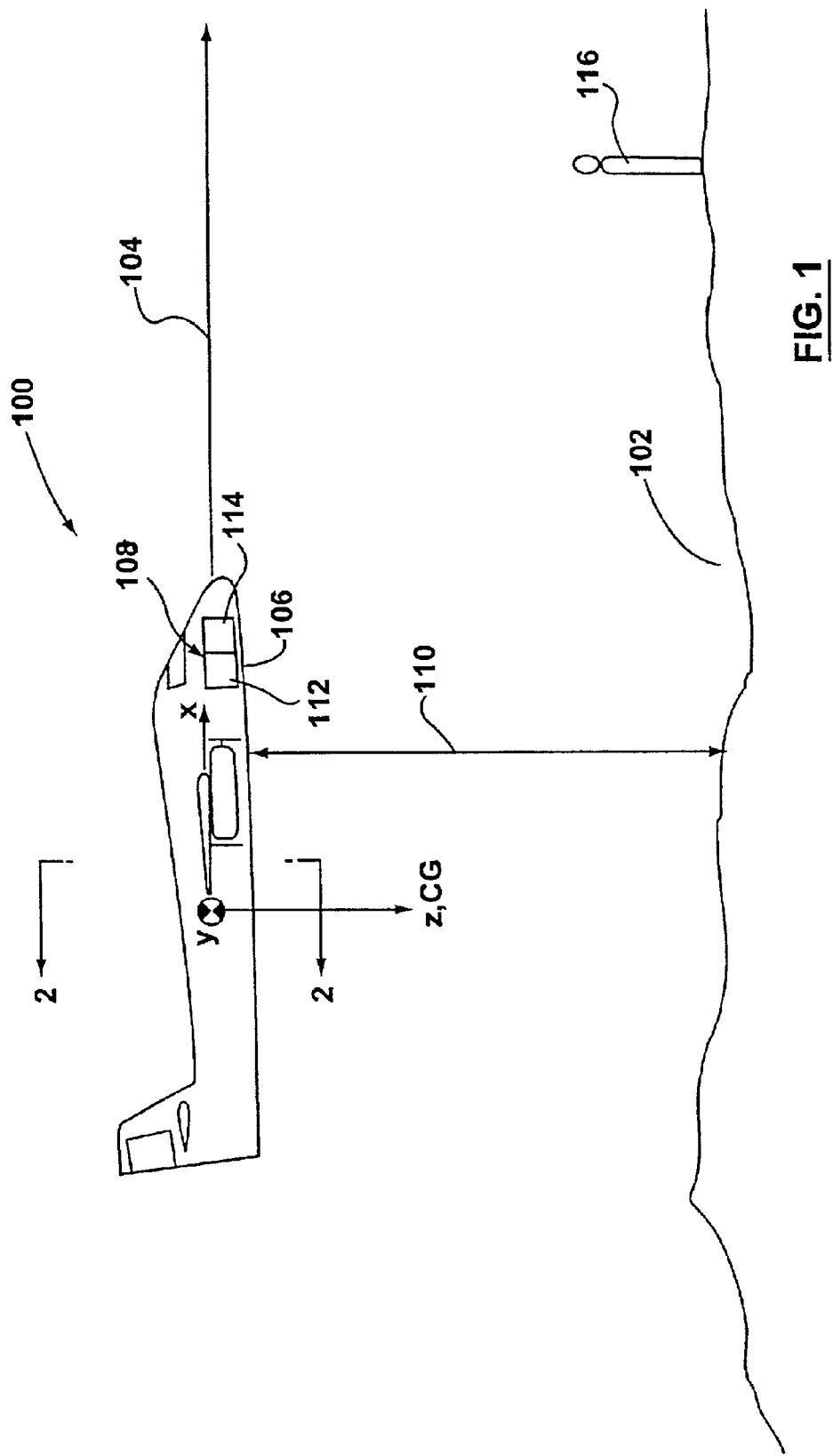
FIG. 1 is a schematic, elevation view of a gravity gradiometer system embodying aspects of the present invention.

FIG. 1 illustrates gravity gradient measuring system 100. System 100 comprises a mobile vehicle or craft 106, illustrated in the exemplary embodiment as aircraft 106, a gravity gradiometer, and a two stage actively controlled isolation mount tailored to the gravity gradiometer and the aircraft. The ideal flight path of aircraft 106 above terrain 102, and more specifically, the ideal movement of a gravity gradiometer carried in aircraft 106, while conducting a survey is path 104. This ideal path 104 is at a constant distance from the center of the earth (i.e., constant altitude) and is of a variable height 110 above the surface of earth 102 owing to the irregularity of the latter.

Figure 1A:
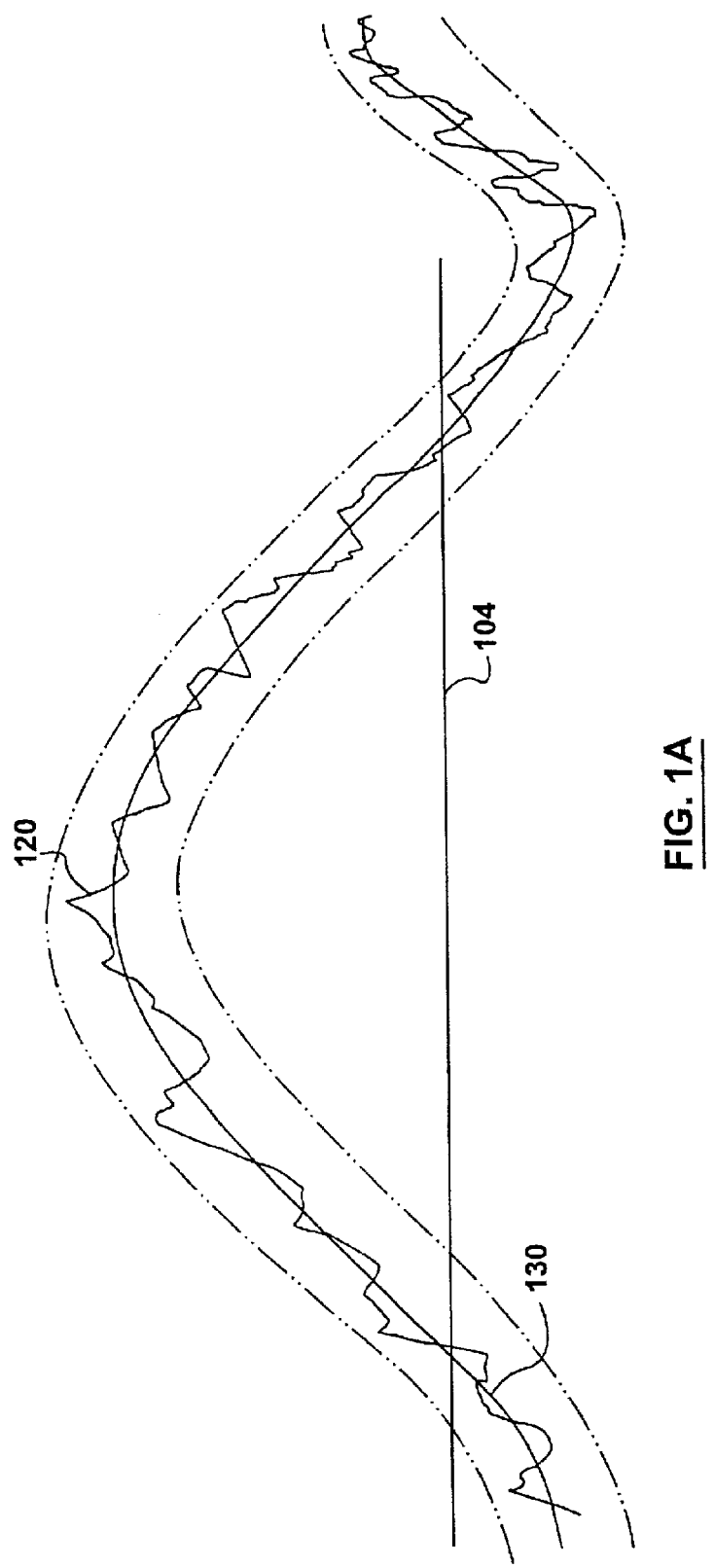
FIG. 1A is a schematic, elevation view of flight paths of parts of the system of FIG. 1.
Figure 1B:
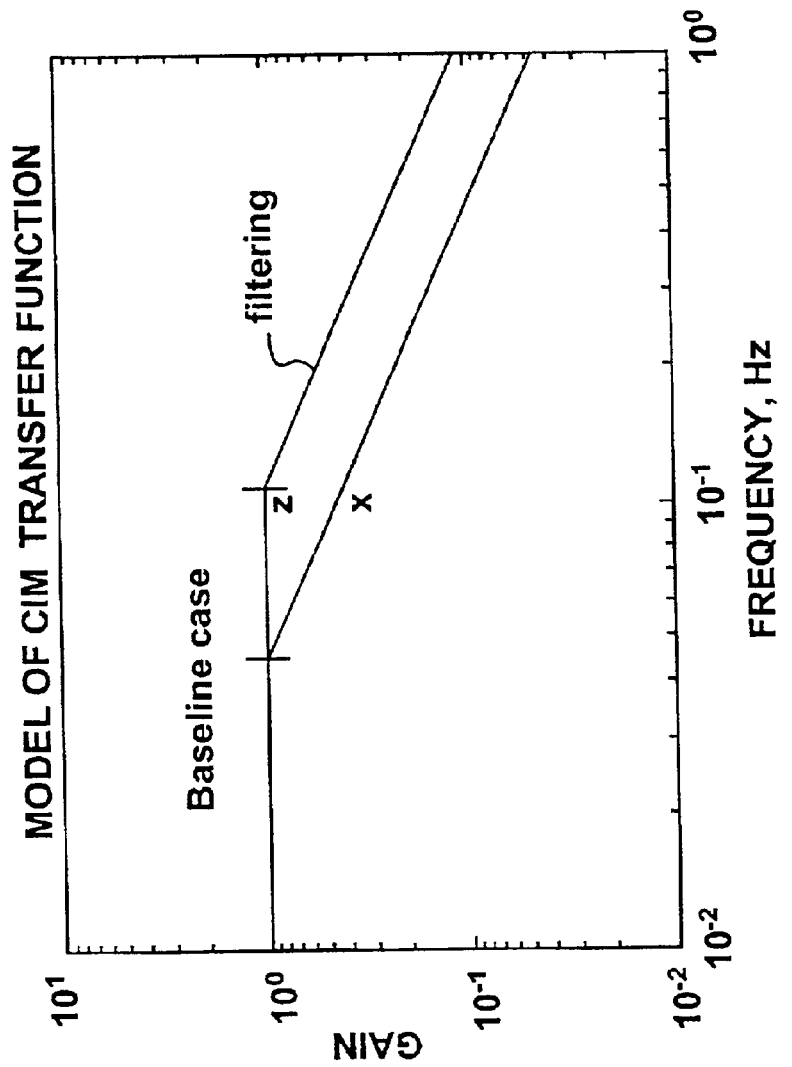
FIG. 1B is a chart illustrating one set of desired ideal isolation performance characteristics for a model isolation system to be used in the system of FIG. 1

With reference to FIG. 1A, ideal flight path 104 is again illustrated. In addition to being the ideal path for the airframe of aircraft 106, it is more accurately the ideal path for a reference point on a gravity gradiometer carried in the aircraft. For flight path 104 to be ideal, the gravity gradiometer should travel path 104 at a constant speed.

However, in actual operation in typical atmospheric conditions, a reference point on aircraft 106 will move along a path like 120. More significantly, the aforementioned reference point on the gravity gradiometer, if there is no isolation system, or if the isolation system is not operating (resulting in the gravity gradiometer being fixed relative to aircraft 106) will travel path 120 or a similar path, unless exceptional steps are taken to provide for enhanced aircraft control. The aircraft will follow path 120 when being controlled by a human pilot or conventional auto-pilot system, such that there will be significant deviations from ideal path 104.

However, if the gravity gradiometer (or a reference point thereon) moves along path 120, there will be significant unwanted accelerations imparted thereon by such movement, which would significantly reduce the signal-to-noise ratio of the instrument, thereby significantly reducing the resolution and accuracy of the instrument.

It has been discovered that if an isolation mount is designed which is specifically tailored to: the characteristics of the aircraft 106; its behaviour in typical survey operational conditions; and to the characteristics of the gravity gradiometer; then the isolation mount can be interposed between the aircraft 106 and the gravity gradiometer, thus causing the reference point on the gravity gradiometer to move substantially along a much smoother path 130 (hereinafter referred to as the gravity gradiometer flight path 130). The accelerations imparted to the gravity gradiometer, if moving along gravity gradiometer path 130, have been found to be acceptably small and will not prevent the gravity gradiometer from producing high resolution gravity gradient information.

As will be appreciated, aircraft 106 can be replaced in alternative embodiments by a land vehicle (e.g., truck, automobile, etc.), or a sea-borne vehicle (e.g., submarine, ship or submersible). In these alternative embodiments, actual flight path 120 and ideal flight path 104 refer to the actual, and ideal three dimensional route taken by the vehicle employed. Gravity gradiometer flight path 130 would also be the 3-D route or path experienced by the gravity gradiometer in these alternative embodiments. Also, many different types of gravity gradiometers can be employed in this invention. In each specific embodiment, the characteristics of the isolation system will have to be specifically tailored to the characteristics of the vehicle/craft, the environment it is operating in, and the gravity gradiometer being employed.

Aircraft 106 can be any conventional air vehicle such as an airplane, a helicopter, a glider, a towed "bird" or a dirigible, that is capable of atmospheric flight. Studies thus far have focused on the De Havilland Twin Otter (also known as the DHC-6)—a well known twin engine aircraft for which much data exists and which exhibits a relatively stable flight platform at low airspeeds of about 100 knots to 150 knots. However, the choice of the DHC-6 for the preferred embodiment was made mostly for convenience, accessibility and reliability reasons. Other aircraft equally suitable for the operations described herein may also be employed.

Throughout this specification reference to an axis system is made. The axis system described herein is one used customarily in flight dynamics with the origin of the axis system located at the center of gravity (CG) of aircraft 106/payload combination, the x-z plane is the vertical plane of symmetry of aircraft 106 with the x-axis pointing in the direction of motion and the z-axis pointing downward. This orientation of the x and z axes defines a y-axis pointing to the right (when viewed from the center of gravity towards the nose of aircraft 106).

Aircraft 106 includes a navigation system 108 which includes both a conventional inertial navigation system (INS) 112 and a conventional global positioning system (GPS) 114 adapted to perform the functions described herein. GPS 114 may be augmented to provide better accuracy through the use of an optional ground beacon 116 in conjunction with the base of differential GPS (DGPS). Navigation system 108 provides flight track data which, when used in conjunction with the gravity gradient measurements provided by system 100, provides accurate mapping of gravity gradients over terrain 102.

As mentioned above, because the atmosphere is not perfectly quiescent, aircraft 106 is not able to follow a perfect level flight path 104 at a constant speed. As a result, aircraft 106 will experience accelerations in all directions. Consequently, a gravity gradiometer conventionally housed within aircraft 106 would also experience these accelerations which would significantly and negatively affect the readings provided by the gravity gradiometer. It has been estimated that a Twin Otter aircraft travelling at an altitude of 150 meters, with a flight speed of 105 knots in turbulence produced by a 20 knot wind would cause a root mean square (rms) vertical acceleration (i.e., ride "bumpiness") on the of order of 0.1 g. Moreover, these accelerations will result in the translation of the aircraft from its ideal level flight path 104, such that it would generally follow an erratic path such as path 120.

Using the gravity gradiometer, e.g., as described by van Kann in U.S. Pat. Nos. 5,804,722, 5,505,555 and 5,668,315, mounted in the aircraft without an isolation system would, in these conditions, result in an estimated spurious signal that could exceed 10 Eö about 50% of the time, and 110 Eö, about 1% of the time. However, on the surface of the earth, a typical 30 megaton ore body at a distance of 1 km beneath the surface will produce a signal only in the order of 1 Eö. As will be appreciated, the desired signal of 1 Eö would be lost or drowned out by the noise caused by the spurious signals. While it is contemplated that the van Kann gravity gradiometers (identified above) will be employed in embodiments of the present invention, other gravity gradiometers could also be employed and will also suffer similar unwanted noise effects to varying degrees.

As discussed above, conventional aircraft with conventional control surfaces, of the class ordinarily used for geophysical surveying, and controlled by a human pilot or a conventional auto-pilot, have flights paths 120 that differ from the ideal path 104. When at the usual low altitude used during surveying, and when the atmospheric wind and turbulence are at the levels usually encountered, the differences between paths 120 and 104 may be several meters. This is the case even when the pilot (human or automatic) uses an optimum strategy to suppress the disturbances.

While it is in principle possible to reduce the difference between paths 104 and 120 to relatively small values by adding complexity to the airplane and to the flight control systems, as discussed hereinafter, in addition to the use of isolation system 206, such changes to the aircraft are beneficial but not necessarily essential when system 100 is employed. System 100 described herein can operate effectively to produce usable gravity gradient data, despite large deviations in flight path by aircraft 106.

As discussed above, the desired ideal flight path for the gravity gradiometer corresponds to constant speed on path 104, in which case it would experience zero disturbances, zero acceleration, and zero acceleration-induced error in the gravity gradiometer. If the gravity gradiometer were "floated" in the cabin, as by a magnetic-levitation active-control system, then it could be made to follow closely the ideal straight trajectory 104, provided that it had sufficient room to move relative to the interior walls of the aircraft.

However, the aircraft movement relative to inertial space can be several meters in extent, and none of the aircraft in the class usually employed for such functions as aerial surveying, have cabins large enough to accommodate such large relative movement of a floating gravity gradiometer system. Frequent hard contact of the gravity gradiometer mount within the aircraft structure would be inevitable. If such contact were to occur, large unwanted accelerations would be transmitted to the gravity gradiometer, resulting in unacceptable errors in the gravity gradiometer signal. Therefore, freely floating the gravity gradiometer is ideal but is not an acceptable practical option.

The opposite of freely floating the gravity gradiometer is to fix it firmly relative to the frame/structure of aircraft 106 (or more likely, fix it firmly with some type of rotational and vibration isolation). In such a case, however, the gravity gradiometer experiences all of the accelerations of the aircraft, and the error introduced in that case can be, as noted above, in the order of 110 Eö. Since the target noise level for the gradiometer is 1 Eö, fixing the gravity gradiometer to the aircraft is therefore not an acceptable option.

The system is designed to reduce acceleration-induced errors in the gravity gradiometer to an acceptable level while at the same time reducing the probability of the gravity gradiometer assembly hitting its stops. Neither fixing the gravity gradiometer to the aircraft, nor floating it freely inside an aircraft can achieve the desired result. In the invention, however, a mounting is featured that lies between the two extremes of fixed and free. That is, the gravity gradiometer is coupled weakly or loosely to the aircraft structure using an active translational isolation mount that comprises two separate components.

The isolation mount is designed to take into account the characteristic spectrum of atmospheric turbulence and the typical response characteristics of a survey aircraft (e.g., the Twin Otter) operating at a typical survey speed.

Studies of aircraft response to atmospheric turbulence reveal the following. At low frequency (below about 0.1 Hz) accelerations are small. However, the displacements are large (in the order of 1 meter or greater) since the time over which the acceleration acts before changing direction is typically long. Above this frequency, the accelerations are relatively large but the displacements are small (in the order of millimeters) because the accelerations act over short time periods before changing signs (i.e., direction).

As a result, an isolation mount needs to be constructed which (1) applies a weak centering force to the gravity gradiometer, to counteract the low frequency, large displacements and to prevent it from hitting the stops (i.e., the physical limits of the cabin space) at low frequency, and (2) act as an active mechanical filter that prevents aircraft vibrations from being transmitted to the gravity gradiometer at higher frequencies.

It should be noted that it is not actually necessary to reduce the accelerations to the point where the gravity gradiometer produces the 1 Eö level directly, since from a combination of analysis and calibration measurements, the function that relates acceleration and bias is known. The instrumentation of the gravity gradiometer system includes measurements of the acceleration components with sufficient accuracy that computation of the required corrections is feasible. A gradiometer output of the order of 30 Eö due to linear accelerations are acceptable, and can be corrected to yield a net output error of less than 1 Eö.

With the translational effects of turbulence reduced by the pilot or autopilot and, if desired, other systems, the gravity gradiometer isolation system 206 (FIG. 2) can be employed within the cabin 220 of aircraft 106 to reduce the unwanted acceleration of gravity gradiometer 600 (described later with reference to FIG. 6) as aircraft 106 moves on its flight path corresponding to path 120. Further, as explained in greater detail below, isolation system 206 also provides for a gentle self-centering force so that a gravity gradiometer used in conjunction with the system is held or moved, with low frequency acceleration, toward its nominal home reference position relative to the aircraft frame and held away from the physical limits or "stops" of isolation system 206. Thus, with use of isolation system 206, the gravity gradiometer (or a reference point thereon) will travel along path 130 and generally be directed towards the home reference position by the isolation system 206. Additionally, in some embodiments of the present invention, the gravity gradiometer isolation system 206 may be in communication with the navigation system (e.g., the autopilot). This communication may be enabled to provide additional data to the navigation system from isolation system 206. This additional data may be used to reduce the difference between paths 104 and 120.

Figure 2:
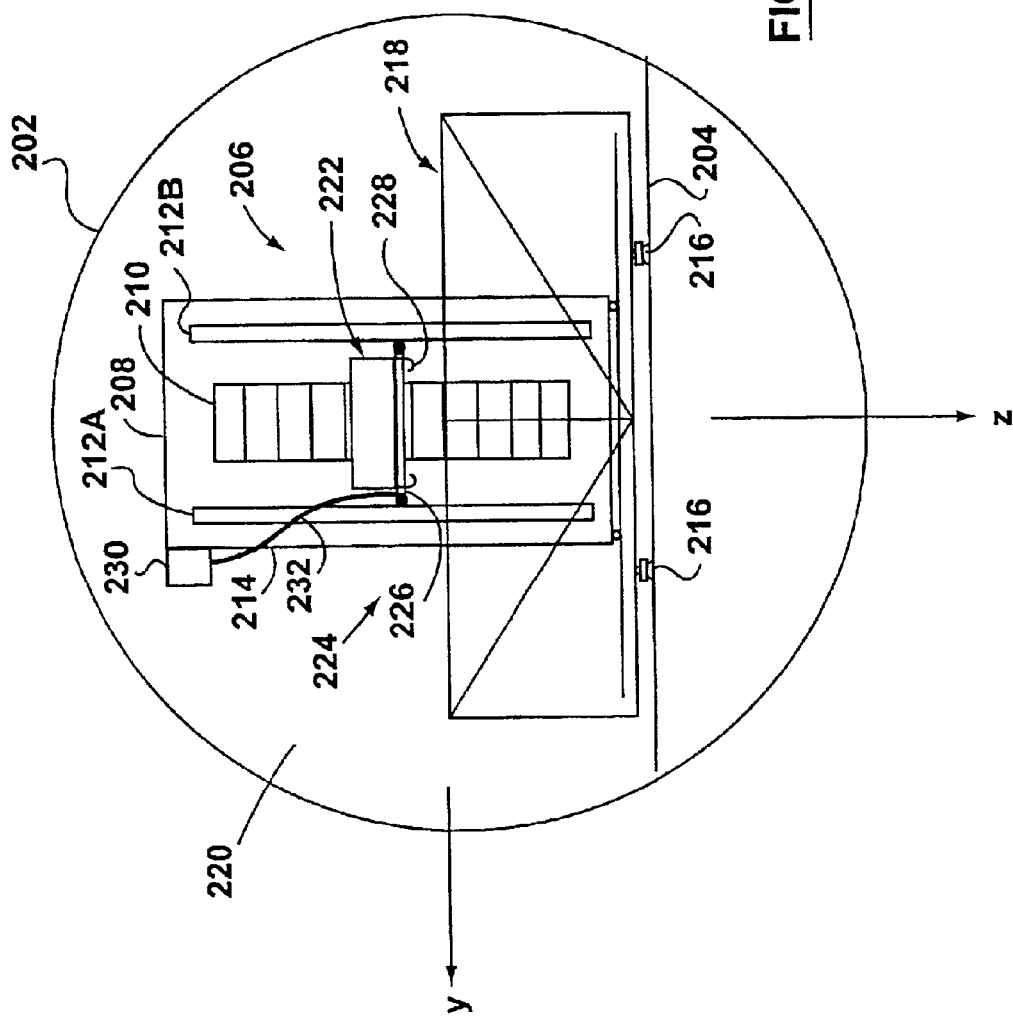
FIG. 2 is a schematic, cross sectional view of a part of an isolation mount of the system of FIG. 1 taken through the cross section 2—2.
Figure 5:
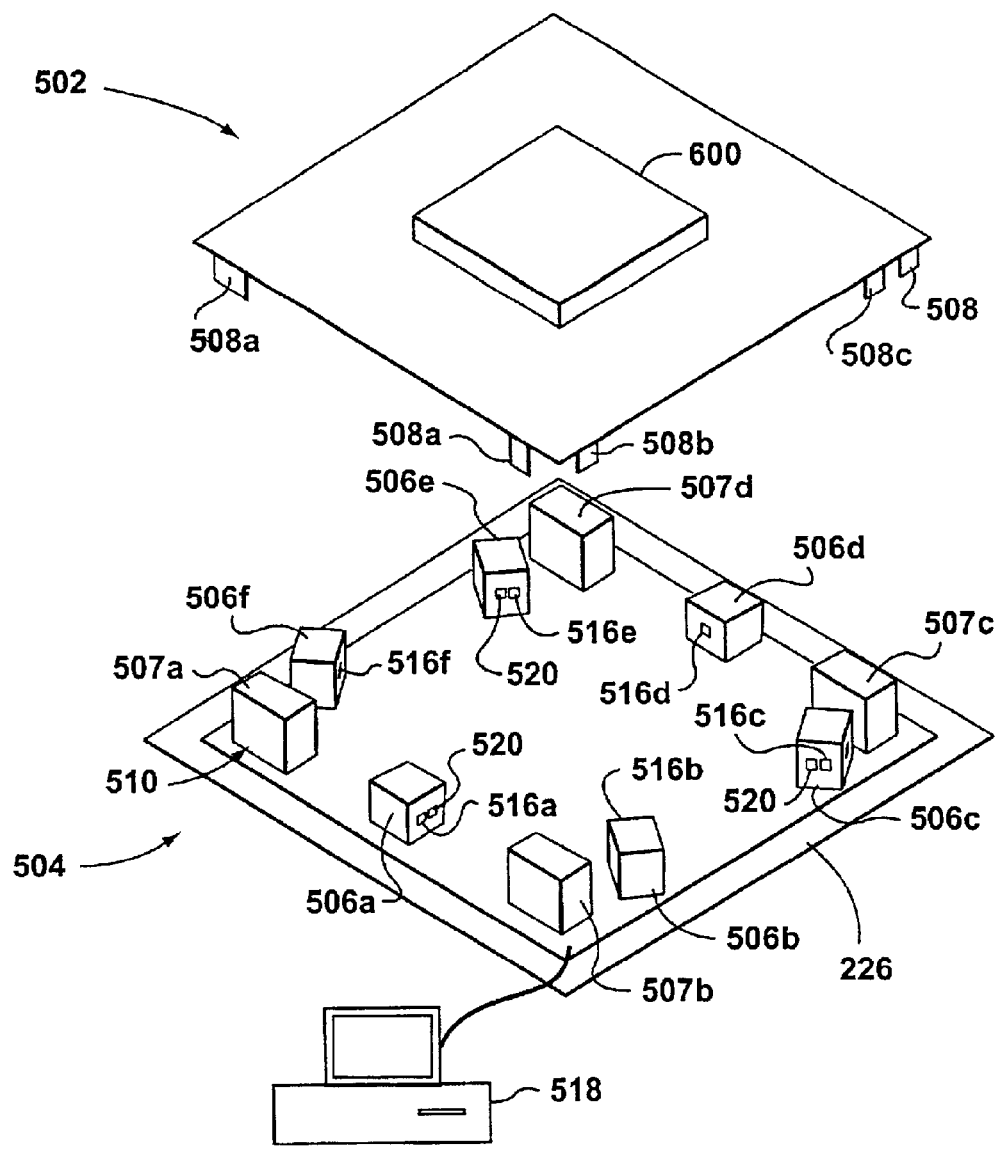
FIGS. 5 and 5A–5E are detailed schematics of a fine motion isolation system mounted to the isolation mount of FIGS. 2, 3, and 4.
Figure 5A:
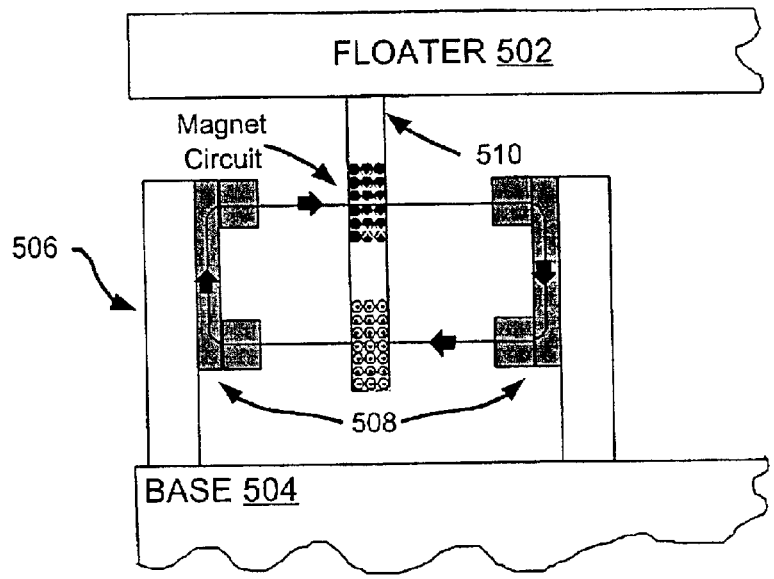
Figure 5B:
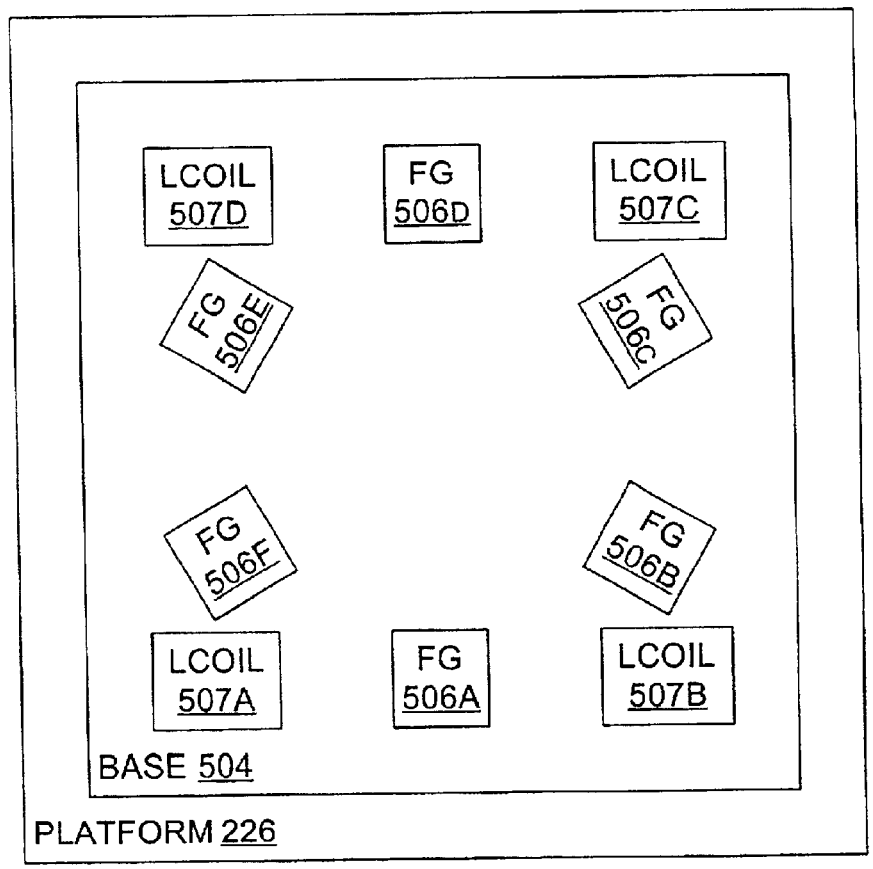

Referencing FIG. 2, isolation system 206 is housed within cabin 220 formed by the fuselage 202 of aircraft 106. Isolation system 206 includes a coarse-stage isolation mount (hereinafter CIM) 224 fixedly mounted to cabin floor 204 which provides for the reduction of inertial translational accelerations, particularly low frequency accelerations, though allowing relative translations of the gravity gradiometer 600 which is carried within aircraft 106 (FIG. 1). Mounted to CIM 224 is fine-stage isolation mount (FIM) 222 which provides for reduction of high-frequency inertial translation and accelerations of the gravity gradiometer, including those introduced by the CIM. Mounted to FIM 222 (as shown in FIG. 5) is the gravity gradiometer 600.

As noted above, aircraft 106 (FIG. 1) will follow a non-ideal flight path 120 due to aerodynamic forces which result from environmental conditions (e.g., gusts, etc.). These aerodynamic forces result in accelerations of the aircraft of order 0.1 g rms. The peaks of the spectrum of acceleration occur at frequencies of about 0.1 Hz. When converting the acceleration spectrum to the displacement spectrum (through a double integration), it is noted that this conversion results in a shift of the peak in the spectrum for displacement to lower frequencies.

The physical consequence of this is that the large displacements, that would cause the gravity gradiometer 600 to bump into the limits of movement imposed by the physical size of the aircraft, occur at low frequency. It is mainly the low frequency content in the acceleration spectrum that generates this aircraft displacement. As long as the displacement is less than the aircraft fuselage dimensions, then the coarse stage platform can be made to follow very nearly the ideal path 104. If the aircraft moves away from the ideal path by more than its own internal fuselage dimension, then the coarse stage will have to impose a force on the platform to move it and the sensor towards the aircraft centerline to keep the instrument package from hitting the aircraft walls, floor or ceiling. This restoring action will include only low frequencies, below 0.1 Hz or lower and the accelerations used will be low enough that the associated acceleration does not introduce significant error and this error can be corrected for.

From further consideration of typical aircraft response it is noted that the low frequency disturbances (i.e., disturbances below about 0.1 Hz in the exemplary embodiment) are characterized by relatively low acceleration levels (of the order of 0.2 m/s$^2$ rms in the vertical, and less in the two horizontal directions), that result in relatively large amplitude translation of the aircraft 106 from the ideal flight path, and that the high frequency disturbances (vibrations) are characterized by relatively large accelerations but small amplitude translation. The fine stage can isolate the gradiometer from the high frequency accelerations.

Recognizing this bifurcation in the frequency regime, CIM 224 has been designed to generally compensate for the low-frequency, large-amplitude excursions of the aircraft. CIM 224 also reduces the likelihood of the gradiometer and its supporting structure from reaching the limits of movement within the cabin of aircraft 106. However, to some extent, CIM 224 will transmit and amplify some high frequency disturbances and allow these to be imparted to the base (226) of the second stage. A reduction or filtering of the effects on the gravity gradiometer 600 of the high frequency vibrations is provided by FIM 222. FIG. 1D illustrates the transfer function of the total isolation system comprising both the CIM 224 and the FIM 222 for both the x and z directions. As a result of the synergistic co-operation between FIM 222 and CIM 224 and preferably, but not necessarily, with the enhanced effects of an advanced flight control system, and by correcting for known measured acceleration errors, gravity gradiometer 600 will experience near zero errors from acceleration and will not impact against the stops at the limits of its physical movement imposed by the cabin of the aircraft 106. Thus, the recognition of this separation of the frequency regime, when combined with the design of a two stage isolation system having separate high frequency and low frequency active control systems, each of which operates independently (and co-operatively), has resulted in a system 100 that provides a suitable flight path 130 for the gravity gradiometer 600.

As illustrated in FIGS. 2 (front view), 3 (side view) and 4 (plan view) of CIM 224 includes three separate translation stages—x-translation stage 216, y-translation stage 218 and z-translation stage 208—one for each of the three orthogonal axes x, y and z. Z-translation stage 208 is mounted to y-translation stage 218 which in turn is mounted to x-translation stage 216. Each translation stage 216, 218 and 208 operates independently to provide three degrees of freedom (3 DOF). Each translation stage is constructed in a similar fashion and provides, in the case of an aircraft, for approximately 50 cm of translation (i.e., $x_{max}$, $y_{max}$ and $z_{max}$ are approximately ±25 cm). While a 3 DOF of CIM 224 is described, other embodiments providing a 1 DOF or 2 DOF system could be employed in alternative embodiments.

Z-translation stage 208, shown most clearly in FIG. 2, includes four parallel low friction rails 212A, 212B (collectively rails 212) vertically mounted to frame 214 parallel to the z-axis. Translatably mounted to rails 212 is support platform 226 which provides support for a payload which, in this case, is FIM 222. Support platform 226 is free to move in the z-direction. Also mounted to frame 214 are linear motors 210A, 210B, 210C, 210D, (collectively 210) which provide motive power to support platform 226. In the preferred embodiment there will be 4 motors for the vertical, one at each corner, to keep the vertical loads symmetric, reducing disturbances. Accelerometers 228 mounted to support platform 226 measure accelerations of platform 226. The acceleration sensed by accelerometers 228 of platform 226 (relative to inertial space) generate signals which are fed into z-control system 230 via z-umbilical cable 232. Z-control system 230 is mounted to frame 214. From the foregoing, it is apparent that the payload for z-translation table 208 is platform 226 (and the gravity gradiometer mounted thereon).

Figure 4:
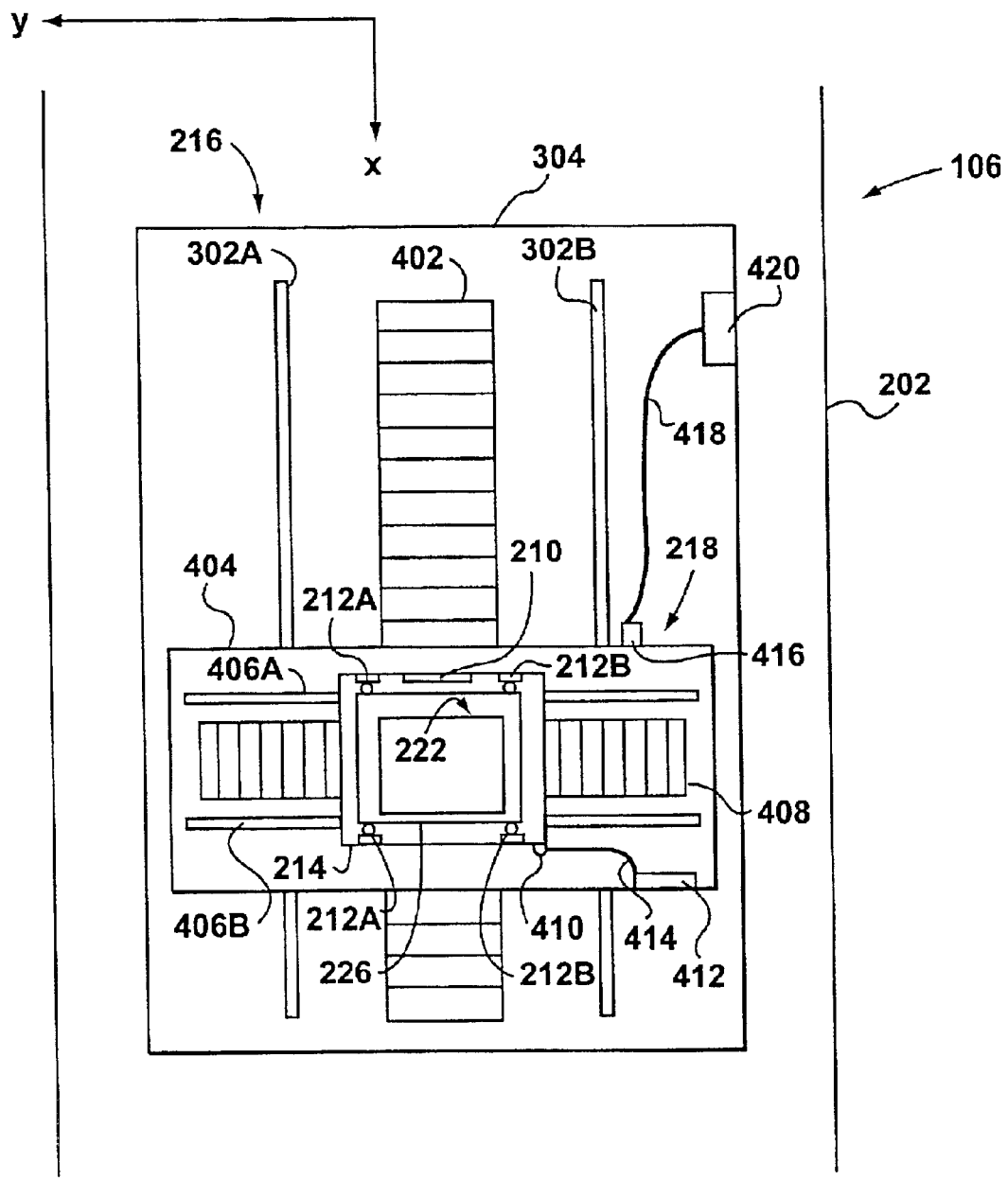
FIG. 4 is a plan elevation schematic of FIG. 3.

Y-translation stage 218, shown most clearly in FIG. 4, includes two parallel low friction rails 406A, 406B (collectively rails 406) horizontally mounted to frame 404 parallel to the y-axis. Rails 406 are similar to rails 212. Translatably mounted to rails 406 is frame 214 of z-translation stage 208 which enables z-translation stage 208 to move parallel to the y-axis. Also mounted to frame 404 is linear motor 408 which provides motive power to z-translation stage 208. Accelerometers 410 mounted to z-translation stage 208 measure accelerations of z-translation stage 208 in the y-direction. The acceleration sensed by accelerometers 410 of z-translation stage 208 (relative to inertial space) generate signals which are fed into y-control system 412 via y-umbilical cable 414. Y-control system 412 is mounted to frame 404. The payload for y-translation stage 218 is z-translation stage 208 and the payload associated with z-translation stage 208.

Figure 3:
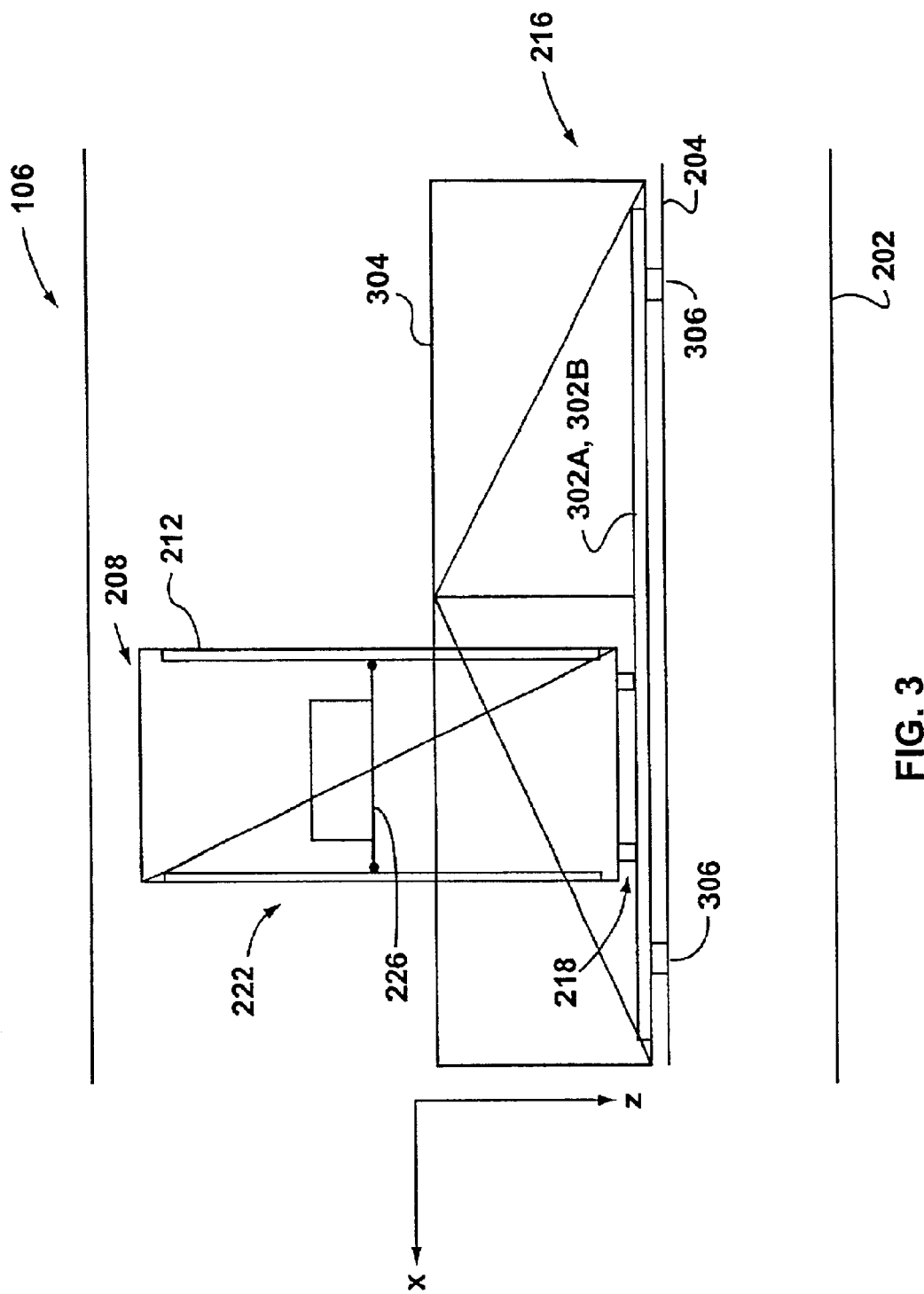
FIG. 3 is a side elevation schematic of FIG. 2.

X-translation stage 216, shown most clearly in FIGS. 3 and 4, also includes two parallel low friction rails 302A, 302B (collectively rails 302) horizontally mounted to frame 304 parallel to the x-axis. Frame 306 is fixedly mounted to cabin floor 204 by conventional mounts such as, for example, bolts. Rails 302 are similar to rails 212 and 406. Translatably mounted to rails 302 is frame 404 of y-translation stage 218 enabling y-translation stage 218 to move parallel to the x-axis. Also mounted to frame 304 is linear motor 402 which provides motive power to y-translation stage 218. Accelerometers 416 mounted to y-translation stage 218 measure accelerations of y-translation stage 218 (relative to inertial space) in the x-direction. The acceleration sensed by accelerometers 416 of y-translation stage 218 generate signals which are fed into x-control system 420 via x-umbilical cable 418. X-control system 420 is mounted to frame 304. The payload for x-translation stage 216 is y-translation stage 218 (and its associated payload—z-translation stage 208 and platform 226).

As will be explained in greater detail below, accelerometers 416 (measuring x-axis acceleration), 410 (measuring y-axis acceleration) and 228 (measuring z-axis acceleration) should be selected so as to provide acceleration measurements accurate to at least 0.001 m/s². Also, linear motors 402 (for x-axis motive forces), 408 (for y-axis motive forces) and 210 (for z-axis motive forces) should be suitable to provide for the application of necessary forces.

The controllers 420, 412 and 230 for the CIM are designed to compensate for any sensed low frequency accelerations; and to compensate for any drag in the system resulting from the friction between a set of rails and the payload mounted thereon, and forces imparted by the umbilical cord. For example, umbilical cord 232 connects platform 226 to control system 230 which is mounted in frame 214. Movement of platform 226 in the z-direction (i.e., upwards or downwards) will result in umbilical cord 232 also being moved. This movement of umbilical cord 232 will impart a resistive force on platform 226 that requires compensation. Compensation for this effect is provided by the z-direction controller. Similar compensation schemes are employed by control systems 412 and 420 (FIG. 4). In addition, controllers 420, 412 and 230 can be used to determine the position of FIM 222 relative to the aircraft 106. Additionally, controllers 420, 412 and 230, using the determined position of FIM 222 relative to aircraft 106, are active to provide the necessary gentle restoring force required to prevent, in most circumstances, FIM 222 from reaching the limits of motion of CIM 224. As outlined in greater detail below in the preferred embodiment, the controllers use position sensing as well as acceleration sensing in the control algorithm.

If desired, wireless communication between the various stages can be employed to reduce the size of the electrical umbilical lines, providing some advantages in the design of the control algorithms. Further, it should be noted that while three independent control systems 230, 412, 420 are illustrated, a person of ordinary skill in the art will appreciate that each of the independent control algorithms could operate in a central processing device. In the preferred embodiment, the FIM controllers can be coupled to CIM controllers.

A system similar to CIM 224 is described in "Development and Performance of a Three Degree of Freedom Large Motion Vibration Isolation Mount for the KC-135" by Tryggvason, B. V., et al., published by the Canadian Space Agency in 1993.

As a result of the arrangement of platform 226 within the nested configuration of z-translation stage 208, y-translation stage 218 and x-translation stage 216, platform 226 is able to translate, independently, in each of the three-orthogonal directions. Further, since each direction table 216, 218 and 208 is controlled independently, platform 226 is provided with three independent degrees of freedom.

In operation, CIM 224 provides compensation for low frequency accelerations and the corresponding large amplitude translation of its payload (FIM 222) so that FIM 222 (or perhaps more accurately, a reference point on the gravity gradiometer) will follow flight path 130 (FIG. 1A). This is accomplished by means of applying a gentle restoring force through activation of the CIM 224, to keep the FIM 222 from reaching the limits of motion of CIM 224 in the cabin. For example, so long as the difference between path 120 (path of aircraft frame relative to inertial space) and path 130—the path of the payload (FIM 222) carried on the CIM 224, does not exceed the maximum available motion of the payload on the CIM 224, then the payload will not contact the motion limits and will avoid any unwanted, associated accelerations.

As described above, low frequency accelerations typically result in relatively large amplitude translations of aircraft 106 (FIG. 1). These low frequency accelerations are measured by accelerometers 228, 410, 416 of z-translation stage 208, y-translation stage 218 and x-translation stage 216, respectively and then compensation is provided by the interaction of the control system with the linear motors of the translation stages of CIM 224.

For example, low frequency motions sensed by position sensors 574 result in signals being transmitted to z-control system 230 via z-umbilical cable 232. Z-control system 230 through, for example, a conventional Proportional, Integral, Derivative (PID) control loop, determines the control signal required to compensate for the z-direction translation of aircraft 106 (i.e., relative positional control). The determined control signal is then transmitted to linear motor 210 resulting in a force being applied in the z-direction to platform 226 to counteract the translations imparted by virtue of the aircraft's z direction acceleration and consequent motion relative to inertial space. Additionally, the accelerometers 228 are used to generate forces on the z translation stage (platform 226) to reduce the reduce the acceleration response of the platform. These latter control forces essentially act to increase the effective inertia of the system. This control approach, which uses a PID control law for relative position, combined with another PI control law based on acceleration is termed the Dual PID (DPID) controller.

Similar compensation for x and y-direction accelerations sensed by accelerometers 410, 416 will be provided by interaction of control systems 412, 420 with the respective linear motors 408, 402 of y-translation table 218 and x-translation table 216, respectively. The DPID controller is not the only possibility as others such as $H_2$, $H_{inf}$, or multi-input-multi-output (MIMO) can be used.

As stated, CIM 224 provides for a low frequency, small amplitude "restoring force" which is used to gently force each translation stage 216, 218, 208 towards its origin or home position, which is a position measured relative to aircraft 106. Accordingly, this restoring force is provided through the relative positional control system. As described above, each translation stage (i.e., x-translation stage 216, y-translation stage 218 and z-translation stage 208) is able to move its respective payload a maximum distance ($\pm x_{max}$, $\pm y_{max}$ and $\pm z_{max}$, respectively) from the origin. This maximum distance is a function of CIM 224 (which typically is sized to provide the maximum translation given the dimensions of cabin 220 of aircraft 106 (FIG. 2)). In the absence of a restoring force, a translation stage, over time, likely will reach its maximum translation and "bump" against the limits of CIM 224. Such a bump against the limits of motion will result in relatively large accelerations being applied to the corresponding CIM stage, and will be directly, and undesirably, imparted onto the payload mounted to or carried by platform 226 of CIM 224.

For example, assuming that without the restoring force z-translation stage 208 had allowed platform 226 to drift upwards towards the ceiling of the cabin 220 aircraft 106 eventually reaching its physical limits (i.e., platform 226 has translated a distance of $-z_{max}$ away from the origin). The contact with the translation stage end stops will result in a shock load being applied to the moving stage with very high (in the order of 1 g or greater) accelerations. Resulting from this acceleration, platform 226 (and thus its gravity gradiometer payload) will experience large accelerations as the payload harshly impacts the physical limits (i.e., stops) of stage 208. It has been estimated through experimentation that the error signal (e) resulting from this situation may be two or three orders of magnitude greater than the gradient being measured.

This type of error is extremely undesirable. Accordingly, to compensate for this situation (i.e., a translation stage allowing its payload to reach the stage's physical limits) each control system (i.e., 230, 412, 420) is designed to impart on the respective translation stage the gentle restoring force referred to above which is used to gently move the translation stage back towards its home or origin position relative to the aircraft.

It is important to note, however that while the gentle restoring force results in a low amplitude and low frequency 'restoring' acceleration, it does not result in a significant error being introduced into the gravity gradiometer operation and, furthermore, compensation for such an error can be performed.

Each individual gravity gradiometer will have its own particular characteristics, including its own error function. The estimated error signal (in Eö) for gravity gradiometer 600 (described below with reference to FIGS. 6 and 6A) follows equation (1).

$$e = 500(E\ddot{o}/m^2/s^4) a_x \cdot a_z \qquad \text{Eq. (1)}$$

($a_x$ and $a_z$ are the accelerations in the x and z-directions respectively in m/s$^2$).

Due to the physical construction of gravity gradiometer 600, the pivot point/planar web (which is in the y-z plane with its longitudinal axis parallel to the y-axis), due to its construction and design, deforms into an S-shaped bend (FIG. 8) during accelerations in the x-direction but remains relatively deformation-free during accelerations in the y or z-direction. As a result of the bending, a rotational error in the bars of gravity gradiometer 600 is induced. The error signal of equation (1) illustrates the coupling of the accelerations in the x and z directions. If the acceleration in one of these directions can be reduced to zero than the error can be effectively reduced to negligible amounts. Error signals resulting from the product of the accelerations in any other acceleration pairs (e.g., $a_x \cdot a_y$, $a_y \cdot a_z$) are, as a result of the design of gravity gradiometer 600 negligible.

Since the gradient desired to be measured is in the order of 1 Eö, those of ordinary skill in the art will appreciate that any error signal induced as a result of a restoring force should be less than the measurement desired (i.e., the measured signal should be greater than any induced noise). As mentioned, the effects of the restoring force and resulting acceleration(s) can be accurately "removed" during data processing. However, in order to minimize the effects of the restoring force, the error resulting from the force applied should be less than the measurement desired (e.g., less than 1 Eö). Accordingly, substituting the gradient measurement desired as the upper limit to equation (1), the error due to the restoring force applied should be less than 1 Eö and, therefore, satisfy the following inequality for the resulting acceleration:

$$500 \, a_x \cdot a_z < 1 \qquad \text{Eq. (2)}$$

$$a_x \cdot a_z < 0.002 \, m^2/s^4 \qquad \text{Eq. (2.1)}$$

As noted above, accelerometers 416 (measuring x-axis acceleration) and accelerometers 228 (measuring z-axis acceleration) should provide acceleration measurements accurate to at least 0.001 m/s². Accordingly, accelerometers 416, 228 have been selected with an accuracy of at least 0.001 m/s². The linear motors 402 (for x-axis motive forces), and 210 (for z-axis motive forces), controlled through the control algorithms, generate restoring forces while maintaining the product of the accelerations less than 0.002 m²/s⁴—which is the maximum acceleration product allowed by equation (2.1).

The restoring force to adjust the relative position of a payload in relation to aircraft 106 to ensure that a payload does not reach the physical limits of a translation stage and is kept close to its home or origin position relative to the aircraft frame is determined as follows. The compensating force applied ($Fc_{rel}$) to adjust the position (relative to the aircraft 106) of y-translation stage 218, the payload of x-translation stage 216, implements the algorithm noted below:

$$Fc_{rel} = k_{pp} \cdot x_{rel} + k_{pd} \cdot \frac{dx_{rel}}{dt} + k_{pi} \cdot \left( \int x_{rel} dt \right) \qquad \text{Eq. (3)}$$

where: $k_{pp}$, $k_{pd}$ and $k_{pi}$ are the proportional, derivative and integral gains for the relative position control, respectively; and $X_{rel}$ is the relative position of the payload (i.e., y-translation stage 218 relative to aircraft 106).

Similarly, corresponding algorithms for the position of a payload in the y and z directions are also applied.

Control Equation (3) is a standard PID controller. As more fully described below, this forms one branch of the complete Dual PID (DPID) control algorithm. The proportional (stiffness) term in Eq. 3 is designed to set the isolation cutoff frequency for the coarse stage, and more generally, along with the derivative (damping) term, the characteristics of the isolation transfer function. The proportional term generates a restoring force that increases as the payload moves further from its home position. This term is tuned to reduce the likelihood of reaching the limits of motion to acceptably low values. If necessary an additional non-linear stiffness term, e.g., through gain scheduling, can be implemented to decrease the probability of contacting the boundary. This can be done in several ways.

The position of a payload in the aircraft frame of reference is measured directly using long stroke displacement sensors. Several types of such sensors are available.

The position control provided by x-control system 420 provides for compensation of low frequency accelerations of aircraft 106 in the x-direction in the relative frame of reference. As indicated above, x-translation stage 216 of CIM 224 includes accelerometers 416 which measure absolute acceleration of the payload of x-translation stage 216 (i.e., y-translation stage 218). Accordingly, to more effectively compensate for the accelerations of the aircraft 106 in the inertial frame of reference in the x-direction, a compensating force in the x-direction ($Fc_{abs-x}$) is applied to y-translation stage 218 through operation of the acceleration control portion of x-control system 420. In the x-direction, acceleration control determines $Fc_{abs-x}$ which in the exemplary embodiment implements the following algorithm:

$$Fc_{abs-x} = k_{ap} \cdot x_{abs} + k_{ad} \cdot \frac{dx_{abs}}{dt} + k_{ai}\left( \int x_{abs} dt \right) + k_{acc}\left( \frac{d^2 x_{abs}}{dt^2} \right) \qquad \text{Eq. (4)}$$

where:

$k_{ap}$, $k_{ad}$ and $k_{ai}$ are the gains proportional to absolute position, to the derivative of the absolute position and to the integral of the absolute position, respectively;

$k_{acc}$ is the gain that is directly proportional to acceleration;

$x_{abs}$ is the translational position, in the inertial frame of reference in the x-direction; and t is time.

Only acceleration in the inertial frame of reference can be measured directly. Accordingly, data signals corresponding to the measured accelerations are, through use of numerical integration, used to generate the remaining terms in accordance with the following:

$$\frac{d^2 x_{abs}}{dt^2} = a_{cc}$$

$$\frac{dx_{abs}}{dt} = \int a_{cc} dt$$

$$x_{abs} = \int \int a_{cc} dt$$

Similar algorithms are implemented by the control system 420 to compensate for translational deviations from path 104 in the y and z directions.

The first three terms on the right hand side of Equation (4) correspond to a standard PID controller based on inertial position. The forth term, i.e., the term set directly in proportion to the measured acceleration, is a term that can be used to effectively increase the mass in the system. This control equation is the second branch of the Dual PID (DPID) controller.

The net force applied to the CIM 224 will be the sum of the restoring force and compensating force, Eq. 3 and Eq. 4 respectively, which should have approximately unity gain at low frequency. The accelerations are subjected to a band pass filter before being used in the control equations. The numerical methods used to calculate the integrals noted above are selected to ensure that growth of round-off errors is contained. Further, error correction schemes can also be implemented so that the error growth is limited to the precision of the computing device implementing the numerical methods for approximating the above noted integrals.

As indicated above, each control system for CIM 224 (i.e., control systems 230, 412, 420) provides relative position control of the position of a payload in relation to aircraft 106. The position control enables compensation for deviations of aircraft 106 from flight path 130.

The effect of the complete controller, obtained through the combination of the control loops defined through Equations (3) and (4) is to reduce the accelerations felt by the payload by guiding the payload along path 130 while the aircraft 106 follows path 120. All of the control gains are set through a single controller design tool to achieve the isolation performance desired. The relative position based terms will tend to dominate at low frequencies to provide the desired centring force, while the inertial terms will tend to dominate in intermediate frequencies to increase the effective mass and to tune the isolation transfer function.

This isolation stage would ideally be sufficient. However, the size of the system is such that it will have its own dynamics, causing less attenuation at frequencies that match the natural frequencies of the CIM. Due to the size of the system the lowest natural frequency will be on the order of 10 Hz. In addition the CIM as shown does not include isolation from rotational motions. These disturbances are resolved by the FIM.

As described above, CIM 224 compensates for acceleration disturbances, i.e., displacements that are particularly in the low frequency regime from about 0.1 Hz to 5 Hz, which tend to generate relatively large amplitude translations of aircraft 106. The frequencies that define this frequency regime may be called "cutoff" frequencies. Notably, there may be some, lesser, attenuation of frequencies outside of the defined regime, however, this attenuation is essentially ignored. CIM 224 may also, by means of restoring forces, attempt to keep any payload away from the physical limits of each translation table and to keep it generally positioned in its origin or home position relative to the aircraft. Synergistically, FIM 222 (illustrated in detail in FIGS. 5, 5A–5F) is suitable to provide reduction of relatively high frequency disturbances, i.e., disturbances above about 3 Hz which tend to generate relatively small amplitude translations of aircraft 106.

A basic auto-pilot is able to reduce airplane rotations caused by atmospheric influences to some degree—down to perhaps 1.2 degrees (20 milliradians (mr)) (rms). A more sophisticated automatic flight control system could do better. Twenty milliradians of rotation is quite high. The rotational gimbals in the van Kann gravity gradiometer for example have a range of movement restricted to about 0.11 degrees (2 mr) on each of the three axes. Thus a basic auto-pilot cannot adequately reduce the airplane rotations and accordingly, isolation from rotations must also be provided. In the preferred embodiment, isolating the gravity gradiometer from the rotations of the airplane is done through the FIM 222. In practice, the relative rotation that must be accommodated by the combination of the CIM 224 and FIM 222 has to be enough to accommodate several times 1.2 degrees (20 mr) to substantially reduce the probability of the limit of rotation of the gravity gradiometer gimbals being reached. For example, if the rotation accommodated by the FIM 222 is 5 degrees (80 mr), then the probability of the limit being reached is small. The actual rotational range that the combination of the CIM and FIM must accommodate will depend on the particular aircraft, the flight control mode, the atmospheric turbulence levels and the use of means to limit the aircraft attitude excursions.

In the exemplary embodiment, therefore, FIM 222 has six degrees of freedom (DOF) and comprises a floater 502 magnetically levitated above a base 504 which is removably mounted to platform 226 of CIM 224. The six degrees of freedom allow for translations along the three orthogonal axes (x, y and z) and rotations about the three orthogonal axes. Six sets of wide gap Lorentz force generators (FG, also called actuators) $506(a)$, $506(b)$, . . . , $506(f)$ (collectively and individually force generators 506) are arranged on FIM 222 to allow for the controlled movement in each of the six DOF. Additionally, four lift actuators (also known as lift coils) $507(a)$, $507(b)$, $507(c)$ and $507(d)$ are arranged to generate a lift of approximately 1 g to counteract the nominal force of gravity thereby allowing actuators 506 to be used to fine tune the control forces. Fixedly mounted to the upper surface of floater 502 is a payload, which in this instance is gravity gradiometer 600. It is contemplated that other fine-stage isolation mounts could be employed in alternative embodiments. The FIM 222 need not operate using magnetic forces. For example, a more passive fine isolation mount, such as a pneumatic support could be employed, but will by itself not have the same performance.

In FIM 222 each force generator 506 (shown in FIGS. 5A–5C) includes magnets 508 (Rare Earth magnets to achieve high magnetic field strength) fixedly mounted to the base 504 and corresponding electromagnetic control coils 510 fixedly mounted to floater 502. Each force generator is independently controllable. Permanent magnets are preferred over electromagnets for magnets 508 since permanent magnets do not require any electrical power supply (and associated cabling). However, permanent magnets 508 could be replaced by electromagnets when used with an appropriate control system which is adapted to compensate for the forces resulting from any electrical and data cabling.

Figure 5C:
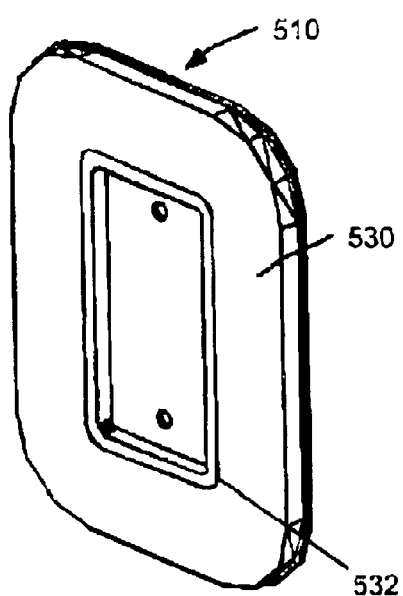

A control coil (or C coil) 510 is illustrated in greater detail in FIG. 5C. As illustrated, the exemplary control coil 510 includes coil wire 530 wrapped around coil spool 532.

The interaction of magnets 508 and control coils 510 is suitable to provide sufficient force to effectively counter any accelerations measured by accelerometers 516 (described below). Lift coils 507 are used to apply a steady vertical load to the payload on the FIM. Control of this steady load is through a separate PID controller using standard high stiffness load cells for sensing the applied load. This vertical load offsets approximately 95% of the weight of the payload. The actuators 506 will provide the remaining vertical force as well as the dynamic control for the isolation function. In the ideal implementation the payload is acceleration free in inertial space. That implies that the total force acting on the payload through the controller is only the nearly constant force required to counter the gravitational force. Deviations from this constant force required from the actuators 506 arise from two main causes: the small acceleration loads associated with the slightly curved path 130 of the gravity gradiometer; and the forces applied onto the floater of the FIM through the umbilical lines. The former load is kept small by the airplane control and by the isolation provided by the CIM. The low frequency accelerations are of the order of 0.05 g, implying loads that need to be transmitted by the FIM of 5% of the weight of the payload. This is well within the load capability of actuators 506. The load applied by the umbilical lines depends only on the displacement of the FIM floater from its home position and on the rate of motion of the floater with respect to the base. Since the umbilical lines are by design very soft, these loads are very low, and easily compensated by the actuators 506. Note that the load does not dependent upon the mass of the payload—the gradiometer 600 and associated structure and the floater 502, other than as described in the foregoing.

Figure 5D:
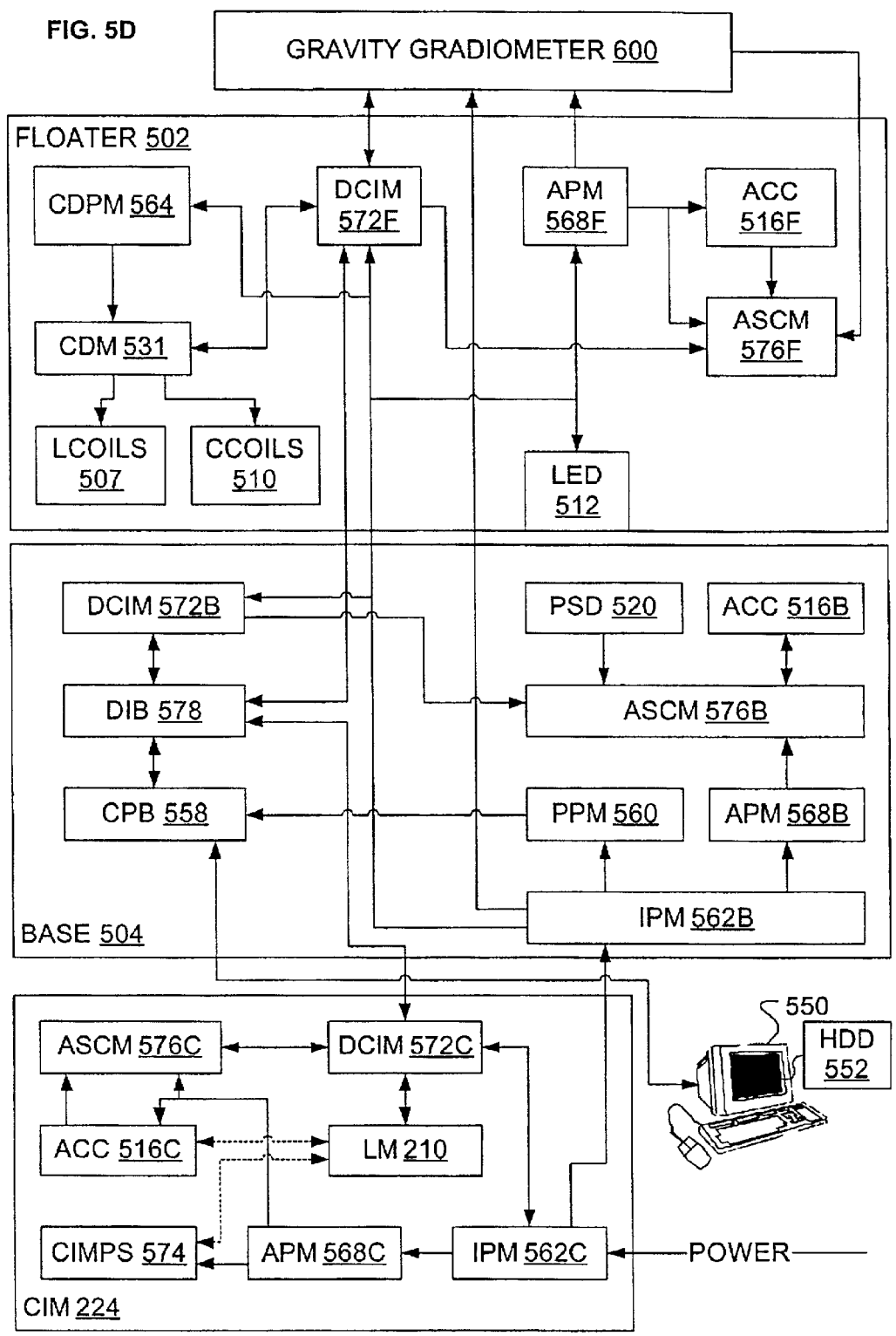
Figure 5E:
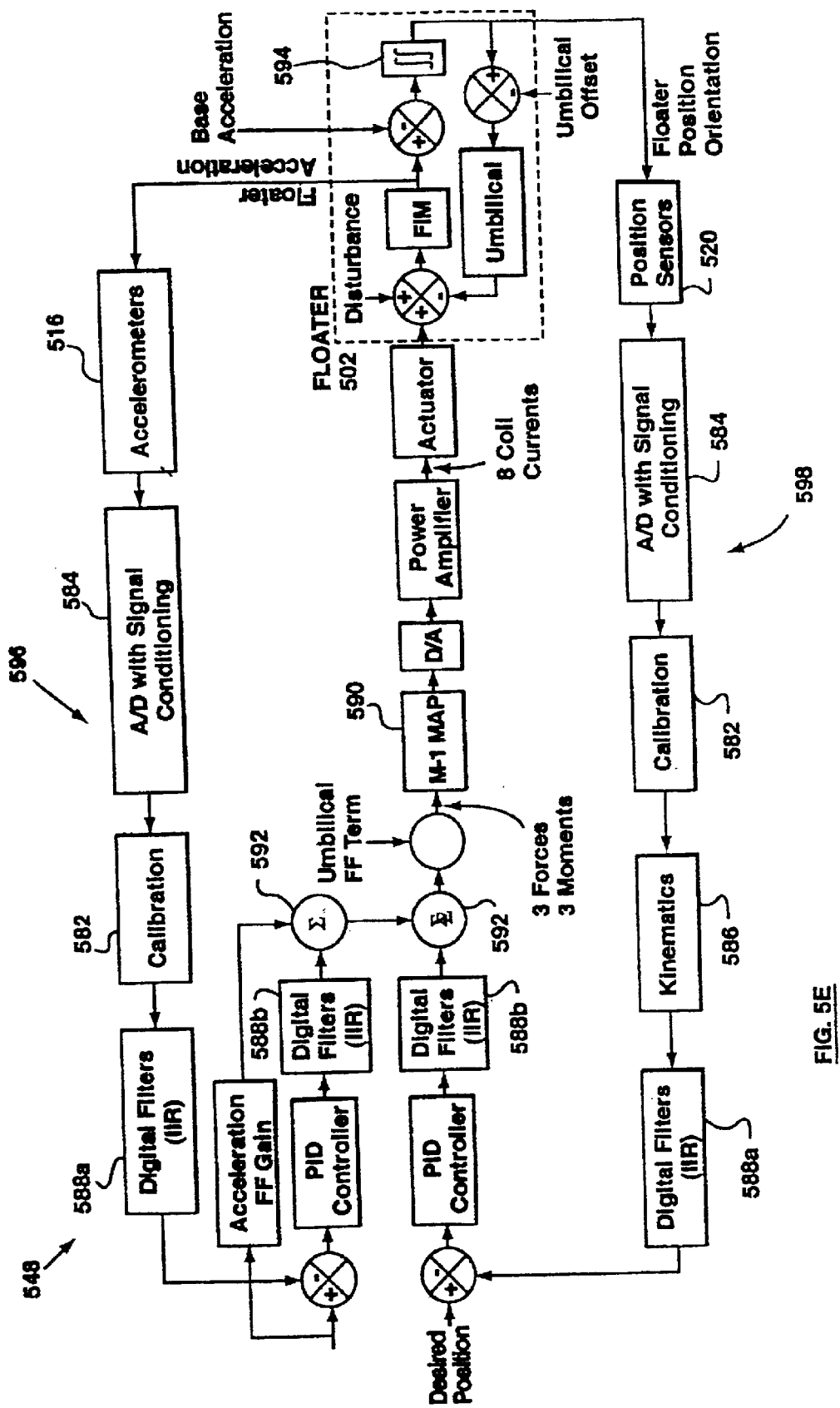
Figure 5F:
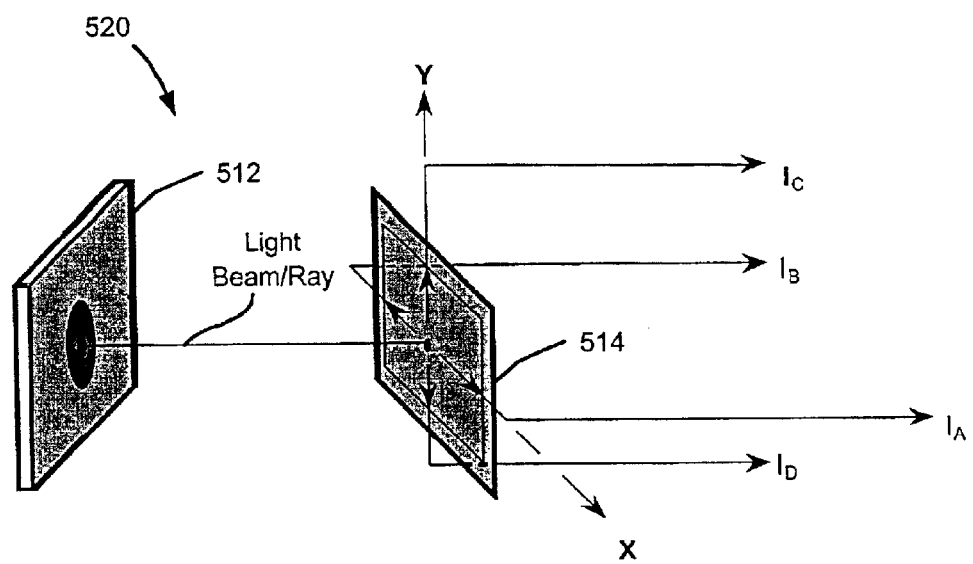
FIG. 5F is a schematic of a position sensing detector forming part of the system illustrated in FIG. 5.

Also mounted to FIM are three position and orientation tracking sensors 520a, 520b, 520c (collectively and individually tracking sensors (or PSDs) 520—and shown in greater detail in FIG. 5F). Each tracking sensor comprises a light sensor 514 and a corresponding light emitting diode (LED) 512. Optimally light sensor 514 is mounted on base 504 with LED 512 mounted on the floater 502.

Light sensor 514 is able to determine the position of light emitted from its corresponding LED 512 relative to the surface of the sensor. As illustrated in the exemplary embodiment of FIG. 5F, light sensor 514 generates four currents ($I_A$, $I_B$, $I_C$ and $I_D$) which depend on the location of the light from LED 512 on the PSD surface. The relative position of the light striking light sensor 514 can be calculated as $x=(I_A-I_B)/(I_A+I_B)$ and $y=(I_C-I_D)/(I_C+I_D)$. In combination, the positions calculated for three tracking sensors 520 can be used to determine the six DOF position (position and orientation) of floater 502 relative to the base 504. Other measurement techniques for determining the six DOF position, such as combinations of capacitive proximity sensors, eddy current proximity sensors, or other optical proximity sensors could be used.

To measure linear and rotational acceleration of the floater 502 relative to inertial space are preferably six accelerometers 516a–f (collectively and individually accelerometers 516) or alternatively three accelerometers and three rotational rate sensors, such as strap down gyros, or piezoelectric gyroscopes. Accelerometers 516 should be suitably selected to measure the accelerations over an appropriate range and at sufficient resolution and accuracy required by the control algorithms used for the CIM 224 (FIG. 1). The accelerations measured by accelerometers 516 may be suitably filtered using conventional techniques. In the exemplary embodiment described herein, accelerometers 516 (and any necessary filtering) should measure a range of accelerations of at least 2 g in the z-direction and 0.5 g in x and y-directions. These ranges are expected to be sufficient in most operating environments. Further, each accelerometer 516 should provide a resolution and absolute accuracy of 1 milli-g (about 0.01 m/s$^2$) for all relevant frequencies and better than 0.1 milli-g (about 0.001 m/s$^2$) for frequencies between 0 and 0.1 Hz. These performance requirements are within the performance envelope of available accelerometers.

An electrical block diagram is shown in FIG. 5D. In data and electrical communication with beach of accelerometers 516 (accelerometers 516F on the FIM floater, accelerometers 516B on the FIM base and accelerometers 516C on each CIM stage), FIM position sensing devices (PSD) 520, CIM position sensors 574, FIM control coils 510 of the six control actuators 506, FIM lift coils 507, and CIM linear motors 210, 402 and 408, is the control processor board (CPB) 558. The CPB 558 is suitable for receipt of data signals from all the sensors and for processing the data through appropriate control algorithms (described below with reference to FIG. 5E). CPB 558, responsive to the processed data, will control and operate control coils 510 and lift coils 507 so as to isolate from high frequency accelerations and is responsive to the processed data and will control and operate linear motors 210, 402 and 408.

The CPB 558 includes a Digital Signal Processor (DSP) (e.g., a Texas Instrument TMS320C40 DSP, reduced instruction set computer (RISC) processor or the like). The CPB 558 interfaces with the system electronics through the Digital Interface Board (DIB) which in turn interfaces with the signal conditioning modules and control output modules through several Digital Communication Interface Modules (DCIM) 572 (DCIM 572F on the FIM floater, DCIM 572B on the FIM base and DCIM 572C on each CIM stage). The CPB 558 communicates with a PC type computer 550 via shared dual port memory to facilitate rapid transfer of data between the computers. The PC computer interface with standard devices such as a monitor, keyboard, mouse and hard disk drive 552.

Processing of the signals from the accelerometers 516, PSDs 520, and CIM position sensors 574 is through high speed, high resolution signal conditioning modules, such as the Accelerometer Signal Conditioning Module (ASCM) 576, including ASCM 576F on the FIM floater, ASCM 576B on the FIM base and ASCM 576C on each CIM stage. The ASCM 576 includes appropriate anti-aliasing filters and analog to digital converters as well as electronics to support digital communications through the DCIM 576. Control signals from the CPB 558 are sent to the various control actuators through the DIB 578, then through the DCIMs 572 and through high resolution, high speed digital to analog (D/A) converters for the control of control coils 510, lift coils 507, and linear motors 210, 402 and 408. In the exemplary embodiment, there are at least two inputs (one for acceleration and one for temperature compensation) for each accelerometer 516, and six outputs (including one for each control coil 510a–f of the six force generators 506a–f—each actuator has only one coil). CPB 558 is, for the control of FIM 222, capable of handling (i.e., receiving or transmitting data on) at least thirty-six analog channels. CPB 558 is further adapted to receive data from gravity gradiometer 600. CPB 558 is also adapted to receive and transmit signals (digital or analog) from/to the respective components of FIM 222 at a suitable rate. Experimentation has demonstrated that, for most expected flight envelopes, a sampling and control rate of 1000 samples/s for each input channel is sufficient as this allows accurate tracking and control up to 100 Hz. For each output channel, a control rate of approximately 100 frames/s (f/s) should be sufficient for most flight envelopes. Software processing allows for lower data storage rates to limit data storage space requirements. The general purpose computer 550 in communication with the CPB 558 is able to read and write from and to a computer readable media 552 (illustrated in the exemplary embodiment as hard disk drive having a capacity for instructions and data storage of several Gigabytes). As will be appreciated by those of ordinary skill in the art, computer readable media can be one or more types of media such as, for example, flash memory, CD-ROM, diskettes, networked drives or the like.

CPB 558 supports DSPs. While CPB 558 is a customized module, commercially available DSP boards could equally be employed. However, CPB 558 eliminates unnecessary (for the present application) components which are often found on commercially available boards and which, as a result of failure, cause the entire board to become inoperative. As a result, CPB 558 provides less chances of failure in harsh environments. The DSP module itself, which plugs into the CPB board 558, is, in the exemplary embodiment, a commercially available Texas Instruments TMS320C40 class processor.

The power modules satisfy the voltage and current requirements for the various electronic components. The power modules include a processor power module (PPM) 560, an input power module (IPM) 562C for the CIM, an input power module 562B for the base, a coil driver power module (CDPM) 564, an analog power module (APM) 568F for the floater, an analog power module 568B for the base and an analog power module 568C for the CIM. As those of ordinary skill in the art are aware, most electronic circuits typically require a combination of +/−12 VDC, +/−15 VDC and 5 VDC which are satisfied by power modules 560–568. As the digital electronics may create electronic noise for the analog electronics, there are two separate paths for converting the direct current input to the current required by the components—one path for the digital boards and another path for the analog boards.

Input Power Module (IPM) 562 acts to provide protection from voltage spikes that are typical on aircraft and further protects the aircraft's systems from problems resulting from the gravity gradiometer system described herein. IPM 562 also acts as a distribution board for the other power modules 560, 564–568.

Coil driver power module (CDPM) 564 generates the most power and variations in power. CDPM 564 is kept separate to minimize generation of electronic noise to the other analog electronics.

In one embodiment, electronics system 518 (FIG. 5) is further adapted to receive positional data from INS 112 and GPS 114 (FIG. 1). Alternatively, the data collected by electronics system 518 from gravity gradiometer 600 may be integrated with flight data from INS 112 and GPS 114 after data collection has ceased (e.g., the survey has been completed) using either electronics system 518 or a separate computer.

As will be appreciated by those of ordinary skill in the art, the components, resolution, sampling or signaling rates and other specifications of electronics system 518 may be modified to accommodate various mission envelopes, accuracy requirements and the like.

The DSP on CPB 558 is programmed to execute a control system for operation and control of FIM 222, CIM 224, and gravity gradiometer 600. The FIM and CIM controllers are of similar complexity. A schematic of the control systems is illustrated in functional block form in FIG. 5E. CIM 224 has a DPID controller wherein relative position tends to dominate for low frequencies (<0.5 Hz) and translational accelerations tends to dominate for intermediate frequencies (0.5 Hz to 5 Hz). FIM 222 also has a DPID controller using relative position and rotation for intermediate frequencies (0.1 Hz to 5 Hz) and linear and rotational acceleration for higher frequencies (1 Hz to 30 Hz). The active control is turned off progressively above 5 Hz for the CIM and above 30 Hz for the FIM. The system design is such that above these frequencies passive isolation is sufficient.

The control diagram 548 provided for the system is illustrated in FIG. 5E. The controllers for the CIM and the FIM and the gravity gradiometer are run in parallel from the same controller code. The design of the control system is linked to the dynamic design of the system. The control diagram illustrates only the essential blocks typical in a control system. The A/D with signal condition block 584 illustrates the amplification and anti-aliasing filter function of the ASCM 576 along with analog to digital conversion. The calibration block 582 illustrates the conversion of measured voltages to engineering units accounting for the calibration of individual input channels. In the determination of the controller gains, the effect of these blocks is accounted for to ensure stability of the controllers.

Digital filters 588 in the input path (filters 588a) are typically Butterworth low pass for the position and orientation and Butterworth band pass for the accelerations. These are set as part of the control algorithm design to optimize the system performance. The filters on the output side (filters 588b) are used for the same reason although their response functions would be set differently. It should be noted that the filtering through each loop is different as the gains in each loop vary in different fashion with frequency.

$M^{-1}$ MAP 590 uses the desired forces and torques that need to be applied through the various actuators as determined by the control algorithms described above, and determines the set of coil currents that need to be generated to obtain this set of forces and torques. Control is typically affected at the center of mass of the isolation stages, including the mass of the payload. Since the center of mass is not co-located with the center of the actuators, the system geometry must be considered in this transformation. In the exemplary embodiment, this system geometry is imported to the software through a data file that is specific to the system.

The summation functions 592 and integration functions 594 illustrated in FIG. 5E are standard symbolic representations of the physics involved in the system. The measured acceleration of the floater 502 is passed to the acceleration control loop 596 (the upper loop of the control system of FIG. 5E). The position and orientation are measured independently. The position/orientation and acceleration are mathematically related through a double integration 594. However, there is no physical integrator in the control loop other than the physical system itself.

Summation functions 592 are, in the embodiment illustrated, performed by the control software. That is, once the control force required is determined by operation of the acceleration loop 596 (the upper loop of the control system of FIG. 5E), and the desired position is determined through operation of the position loop 598 (the lower loop of the control system of FIG. 5E), these are added together by summation functions 592 (one for each of the acceleration loop 596, position and orientation loop 598 plus a term for the forces imparted by the umbilical cords 232, 414 and 418) to obtain the total force required.

Figure 6:
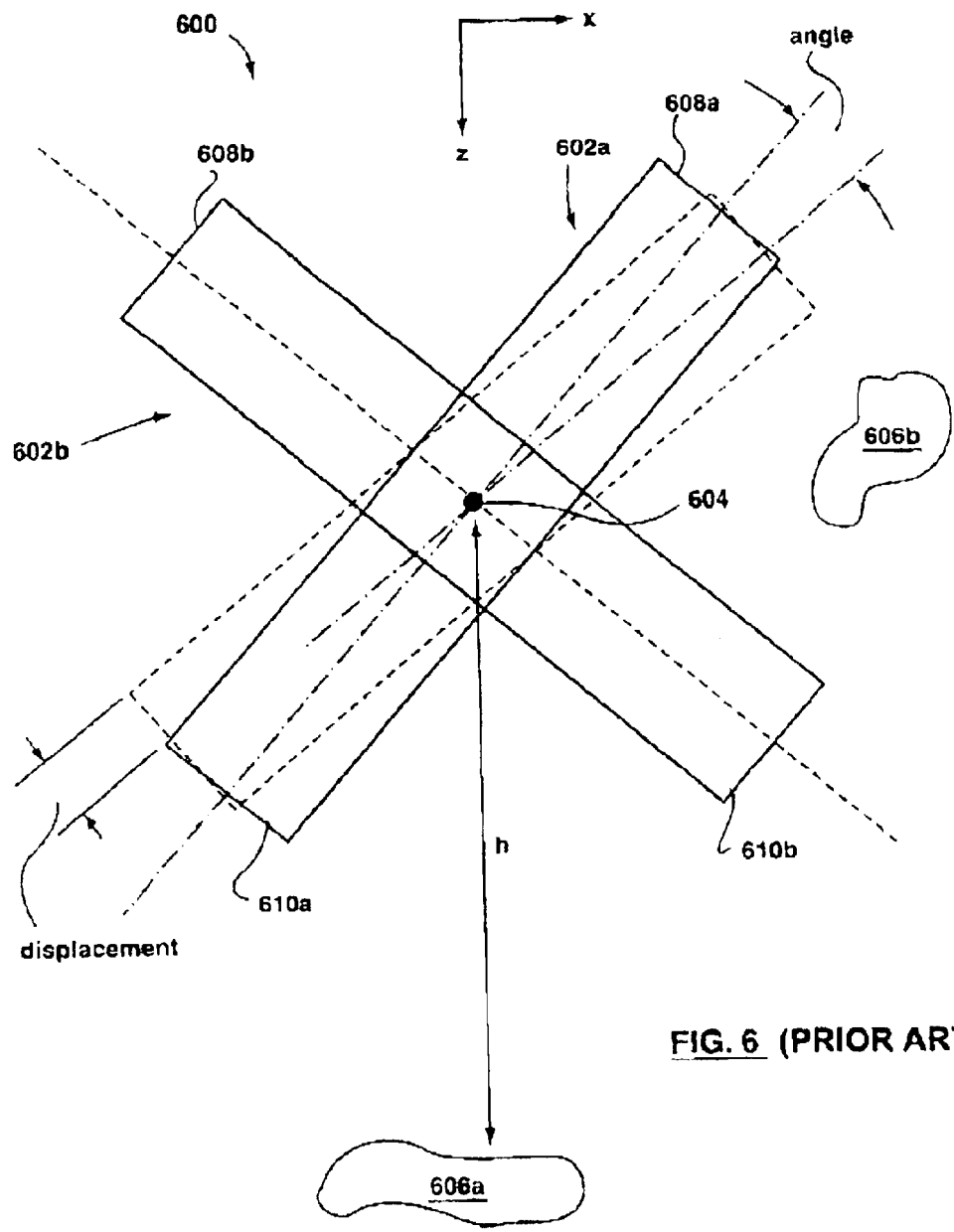
FIG. 6 is schematic of a gravity gradiometer housed within the fine motion control system of FIG. 5.

FIG. 6 is a symbolic illustration of a crossed dumbbell gravity gradiometer 600. Gravity gradiometer 600 includes a pair of "scissor" bars 602a, 602b rotatably mounted to pivot 604. Although rectangular bars are shown for illustration purposes, the bars may be of a different shape. Each bar 602 includes an upper end 608 and a lower end 610. When not subject to a gravity gradient (i.e., in equilibrium), bars 602a, 602b are at right angles to each other. Additional details to a selected embodiment of the gravity gradiometer employed within the invention can be obtained from embodiments of the van Kann patents identified above. The specifications of bars 602 have been selected to, when combined with the other elements described herein, detect a gradient of 1 Eö. However, and as will be appreciated by those of ordinary skill in the art, modifications to these specifications can be made to enable different missions and flight envelopes to be pursued.

Figure 6A:
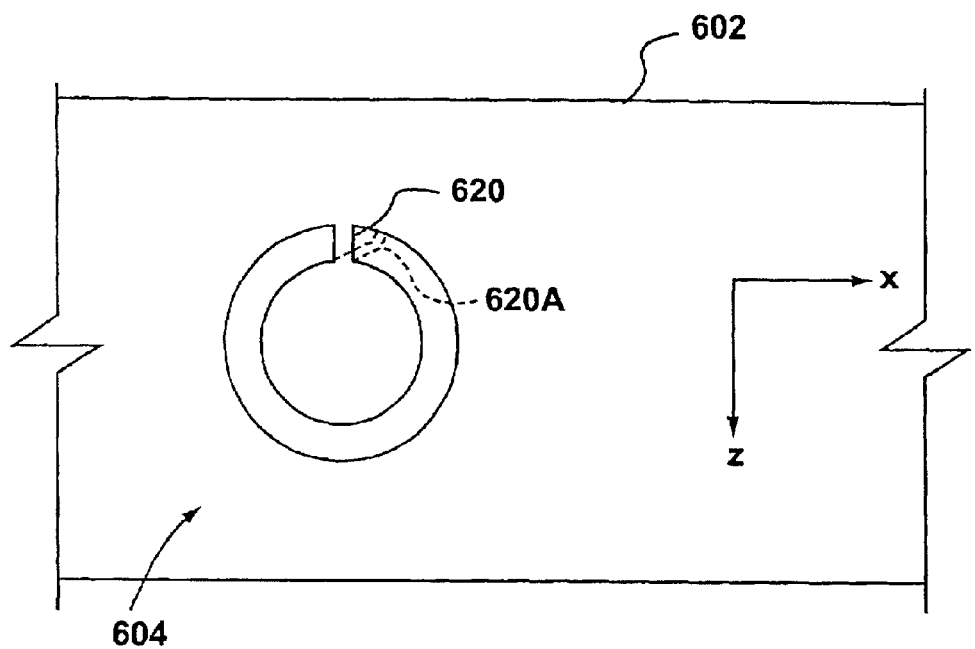
FIG. 6A is a schematic side view of a portion of the gravity gradiometer of FIG. 6.
Figure 6B:
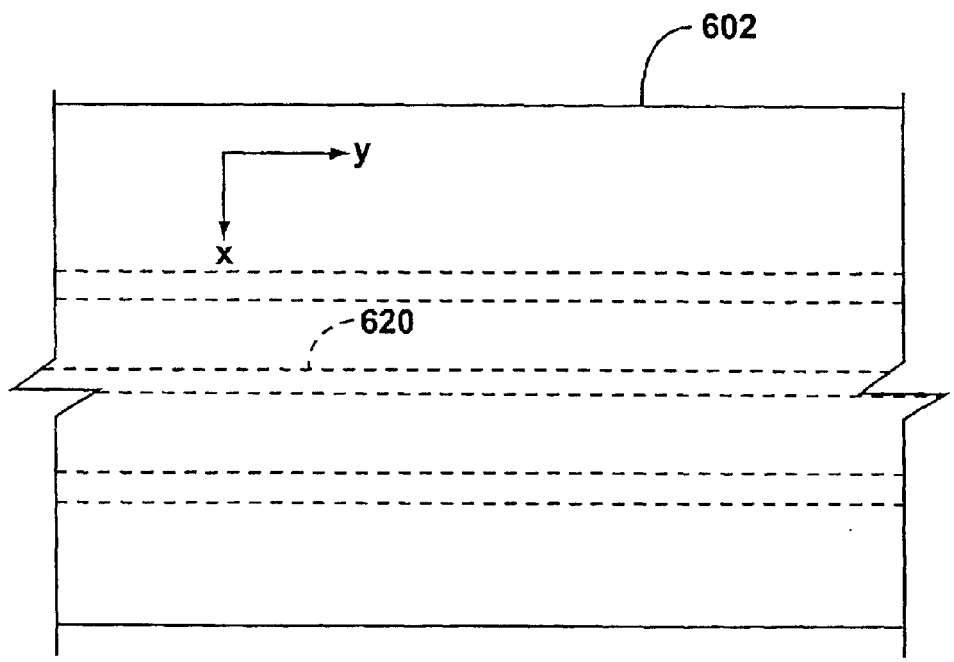
FIG. 6B is a schematic plan view of a portion of the gravity gradiometer of FIG. 6.

A mass anomaly, such as either of masses 606a or 606b, will cause bar 602a and 602b to rotate about pivot 604 such that the ends closest to, and farthest from, the mass anomaly 606 will move closer together. Pivot 604 is shown in greater detail and in perspective view in FIG. 6A and in plan view in FIG. 6B. As shown in FIGS. 6A and 6B, the web 620 is relatively dimensionally thin in the x-direction as compared to the y and z-directions. As a result, accelerations in the y and z-directions imparted on gravity gradiometer 600 will cause relatively little deformation of web 620. However, due to its dimensions, web 620 will be deformed (to extent that results in erroneous signals) when gravity gradiometer 600 is imparted with x-direction accelerations. An exemplary deformation caused by a positive x-direction acceleration is shown in dashed lines in FIG. 6A as deformation 620A and can also be readily understood from FIG. 8.

The rotation of a bar 602 is inversely proportional to the cube of the distance from the mass anomaly. The linear displacement (indicated by "à") of a bar end (e.g., lower bar end 610a) from its equilibrium position (shown partially in dotted outline) can be measured and used to determine the rotation ("Ë") of the bar from its equilibrium position.

For mass anomaly 606a, lower ends 610a, 610b will move towards each other. Similarly upper ends 608a, 608b will move towards each other—an indication of a gravity gradient $G_{zz}$. However, mass anomaly 606b will result in lower end 610b moving closer to upper end 608a. Similarly, lower end 610a and upper end 608b will move towards each other—an indication of a gravity gradient $G_{xx}$. As will be appreciated, mass anomaly 606b will cause lower bar ends 610a, 610b, and upper bar ends 608a, 608b to move apart from each other—directly opposite to the effects caused by mass anomaly 606a. Consequently, gravity gradiometer 600 is adapted to measure $(G_{zz}-G_{xx})$.

Although only one gravity gradiometer 600 measuring $(G_{zz}-G_{xx})$ is illustrated as being mounted to platform 226 (FIG. 2), additional gravity gradiometers similar to gravity gradiometer 600 but mounted in alternative orientation so as to measure one or more of $(G_{zz}-G_{yy})$, $(G_{xx}-G_{yy})$ could also be employed. It is contemplated that other designs and types of gravity gradiometers could also be employed. However, it was discovered that particularly powerful synergies between the crossed dumbbell type of gravity gradiometer 600 and the translational isolation system 206 and the relative dimension and characteristics of most mobile vehicles, particularly an aircraft, could be advantageously employed if the embodiment described above is used. First, due to the shape of a typical aircraft cabin, room for translation of the CIM is largest in the x-direction, with less room to the cabin walls in the z and y-directions. To take advantage of this, the CIM for an aircraft can be built with a translational capability or limits of movement much greater in the x-direction versus the z or y-directions (limits dictated by the dimensions of the aircraft cabin). This is combined with the observation that accelerations and the resulting displacement due to turbulence etc. in the x-direction are relatively small and easier to control. Furthermore, compensation for accelerations in the x-direction are the most critical to attenuate for the van Kann dumbbell design for measuring $G_{zz}-G_{xx}$, as explained above. Consequently, in a mobile vehicle such as an aircraft, the combination of the translational isolation system with a gravity gradiometer of the van Kann dumbbell design for measuring $G_{zz}-G_{xx}$, both described in greater detail above, allows the gravity gradiometer to be most effectively sheltered from the specific accelerations that are the most detrimental to performance. The invention minimizes dominating acceleration-induced errors, and the above combination design specifically takes advantage of various synergies to minimize the most important accelerations and get the maximum benefits when considering the '$G_{zz}-G_{xx}$' embodiment. Finally, it is recognized that although other gravity gradient components can be measured, the utility of $G_{zz}-G_{xx}$ is such that it can provide powerful information and therefore if desired, a single component system can be employed to take advantage of the discovered synergies above without the design effort required to include the measurement of other components.

If 606a is a thirty megaton ore deposit at a distance ("h") of 1 km from gravity gradiometer 600 (ignoring, for a moment, mass 606b), a linear displacement (à) of approximately $1 \times 10^{-13}$ meters will occur and be detected. This linear displacement translates, for the exemplary gravity gradiometer 600, into a rotation (Ë) of approximately $3 \times 10^{-13}$ radian.

Referring to FIGS. 1–6, in operation aircraft 106 of gravity gradient measuring system 100 will take off from a runway with isolation system 206 in a stowed or locked position. In the stowed or locked position, the translation tables of CIM 224, the magnetic levitation system of FIM 222 and gravity gradiometer 600 are in a fixed state so as to prevent any damage that may occur during takeoff. Prior to landing isolation system 206 is returned to the locked or stowed position for the same reason.

Once airborne, aircraft 106 will travel to the area where the gravity gradient survey is to be conducted. At this point, the auto-pilot or human pilot system of aircraft 106 is employed to begin a survey. The auto-pilot system may be programmed to follow a flight path so as to fully survey an area. Once in the position where surveys are to be conducted, isolation system 206 is energized allowing the translation tables of CIM 224 and the magnetic levitation system of FIM 222 to operate as described above. Moreover, navigation system 108 of aircraft 106 will also begin recording data identifying the actual flight path 120 traveled and, by incorporation of the CIM and FIM relative position and orientation data, identification of the gravity gradiometer flight path 130. As indicated above, this flight path data will be, typically after a flight survey has been completed, collated with the gravity gradiometer measurements taken so as to generate a gravity gradient map which overlays the gravity gradiometer data on a conventional geographical or geopositional map (which may be in two or three dimensions in printed or electronic format). In an alternative embodiment, navigation system 108 may transmit data directly to isolation system 206 during flight. In this alternative embodiment, the gravity gradient and navigation data may be collated in real time, near real time or at a later point in time.

As indicated above, while aircraft 106 travels along actual flight path 120, aircraft 106 is being perturbed from ideal or desired flight path 104. The autopilot system, in co-operation with navigation system 108, can attempt to reduce these perturbations through the measures and means described above. Advanced avionic control systems might be able to keep the path of aircraft very close to path 104. However, as will be appreciated by those skilled in the art, these perturbations are extremely difficult to reduce to the levels required by gravity gradiometer 600. Accordingly, accelerometers 416, 410, 228 of CIM 224 measure any accelerations throughout the frequency regime. This data is filtered and compensated for by CIM 224, particularly lower frequency accelerations. The acceleration data received from accelerometers 416, 410, 228 is used by the controllers of CIM 224 to determine any large amplitude, low frequency translation of aircraft 106. Using this acceleration and translation data, CIM 224 will adjust the position of the translation stages so that the gravity gradiometer 600 will continue to move along smooth path 130 at a substantially constant speed (i.e., the same speed as the average speed of the aircraft 106).

The translations imparted by CIM 224 result in FIM 222 being kept away from the extreme limits of travel made available by CIM 224 (i.e., FIM 222 may reach one or more of the physical limits—$\pm x_{max}$, $\pm y_{max}$ and $\pm z_{max}$—of CIM 224). This action is accomplished by the controllers of CIM 224 actively tracking the position of the payload of each of the three translation stages 216, 218 and 208 and, as discussed, applying a weak "restoring force" which results in the various payloads being directed toward their respective home positions. As a result of the restoring forces applied, the payloads of translation stages 216, 218 and 208 will, during most flight envelopes, not reach the physical limits of CIM 224. Consequently, FIM 222 and gravity gradiometer 600 are able to operate without severe accelerations being imparted on these devices as a result of repeated impacts against one or more of the physical limits of CIM 224.

As a result of the interaction of the flight control (human or autopilot) system and navigation system 108 of aircraft 106 and CIM 224, the accelerations of the gravity gradiometer and FIM 222 as it travels on the flight path 130 are substantially reduced compared to the accelerations of the aircraft frame as it moves along flight 120. In fact, FIM 222 (or more accurately, the portion of FIM 222 mounted to CIM 226—base 504) will, as a result of the interaction and operations described above, typically only experience small, high frequency (greater than about 1.0 Hz) amplitude accelerations (and the small amplitude translations which result therefrom).

During operation, FIM 222 synergistically provides for the reduction of high frequency accelerations in six degrees of freedom through operations of its magnetic levitation system. Accelerometers 516, as described above, measure accelerations in six degrees of freedom of the base 504 relative to inertial space. The accelerations measured by accelerometers 516 are then used in conjunction with the position sensors 520 and the control system implemented by electronics system 518 to apply a force, through control and operation of Lorenz force generators 506, to floater 502 which counteracts the small amplitude, high frequency accelerations experience by base 504.

The tracking of the floater 502 relative to the base 504 is used by the control system of FIM 222 to ensure that a force is not applied that would result in the floater 502 reaching any of its physical limits of movement within the confinements of the base 504.

The FIM 222 will operate to reduce high frequency, small amplitude accelerations in six DOF of the floater 502 and its gravity gradiometer payload 600.

Upon completion of the flight, data corresponding to gravity gradients measured (gathered from gravity gradiometer 600) and the position of where these measurements were taken (gathered from navigation system 108) has been collected. Additionally, the amplitude and direction of any restoring forces applied, and the time or position when these restoring forces were applied has also been recorded. Additionally, self-mass correction data may be used. The self-mass correction data, which may be generated prior to, during or after the flight, identifies the effects of the mass distribution of the aircraft, its systems, its fuel, instrumentation and equipment carried therein, and the position of people, etc. (and, if desired, the change in these factors) which impact or affect the data collected by gravity gradiometer 600. Additionally, data corresponding to the terrain or topography over which vehicle 106 travelled may also be employed. The topographical data may be collected through use of a laser altimeter forming part of the systems of aircraft 106 (or the equivalent thereof—e.g., radar, topographical maps, etc.). The data collected and employed can then be collated to generate a two or three dimensional "map" of the gravity gradient over a terrain. From this map, and using conventional techniques, significant geological structures and the like, which result in gravitational anomalies can be identified.

Although system 100 can function to provide usable data from gravity gradiometer 600, enhancements could be made to the aircraft control system. For example, feed forward control algorithms using gust sensors to detect on-coming gusts combined with known flight characteristics of the aircraft can be used to adjust the aircraft to further reduce the effects of the detected gusts. The control systems (either feedback or feed-forward, individually or in combination) may then be used in conjunction with conventional autopilot systems to approach the ideal flight path 104. Additionally or alternatively, modifications to the aircraft itself could be employed to provide for enhanced control of the movement of the aircraft. These modifications may include, for example, direct lift control (DLC) using common mode ailerons, variable spoilers, fast-acting flaps or even the free wing concept, to provide for enhanced vertical (i.e., z-direction) motion compensation and control; variable drag control through body or tail-stinger mounted variably deployable drag surfaces, propeller pitch or throttle control, to provide for enhanced forward (i.e., x-direction) compensation and control; ventral fins, differential engine thrust control (for twin engine aircraft), ventral wing-tips or rudder fins, could be employed to provide for enhanced lateral motion (i.e., y-direction) compensation and control.

As a further alternative, control signals can be received by autopilot/navigation system 108 from isolation system 206.

In review then, a measuring instrument is combined with a two-stage actively controlled motion isolation system. The instrument and two stage isolation system may then be mounted within (or on) a mobile vehicle such as, for example, an aircraft. The first stage of the two-stage system provides a low pass motion isolator, that is, a stage that allows low frequency motion (i.e., motion at a frequency less than a cutoff frequency of the first stage) to be passed through the system from the mobile vehicle to the second stage and on to the instrument, which may be a gravity gradiometer, mounted to the second stage. The first stage progressively attenuates motion having a frequency above the cutoff frequency of the first stage such that the second stage and instrument respond less and less to motion as the frequency of the motion increases above the cutoff frequency. An ideal first stage requires no further isolation, as the first stage ideally isolates from motion at all frequencies above the cutoff frequency.

However, there are practical limits on what may be built. The first stage, in order to isolate very low frequency motion, may be quite large and, because of its size, may have associated dynamics characterized by vibration modes with, assuming a good design, a lowest natural frequency of about 10 Hz, and many more modes at frequencies above this. These modes are likely to be driven into vibration. To isolate the instrument from these vibrations, a second stage isolator is used, which, being much smaller, can be designed such that the natural frequencies are quite high, of the order of 100 Hz. The second stage is a low pass vibration isolation system, which isolates the instrument from frequencies above the cutoff frequency of the second stage. The cutoff frequency for the second stage may be set, while designing the motion isolation system, to be above the cutoff frequency of the first stage, but below the frequency for the lowest natural frequency (also known as the first dynamic mode) of the first stage.

In use, a gravity gradiometer may be mounted to a two-stage actively controlled motion isolation system and used in geological surveying to measure the Earth's gravitational acceleration. By repeating the measurements at many locations, a map of the gravitational acceleration can be obtained, which can then be used to locate geological features. These geological features may include a mineral deposit, a volume of gas, a volume of fluid, a tunnel or other cavity, a porous media containing a gas, a porous media containing a fluid and an artifact, such as a submarine or sunken vessel.

Other modifications will be apparent to those skilled in the art and, therefore, the invention is defined in the claims.

What is claimed is:

1. A gravity gradient measuring system for use in an aircraft comprising:
   (a) a gravity gradiometer for mounting in an aircraft;
   (b) a coarse stage isolation mount for mounting in an aircraft for attenuating first displacements of the gradiometer relative to a flight path ideal to the measurement of gravity including:
      (i) a platform;
      (ii) translation stages supporting said platform for movement along three orthogonal axes, whereby said translation stages isolate said platform from low frequency, first displacements of the aircraft along any of said three orthogonal axes in response to turbulence, thereby minimizing the acceleration of said platform relative to inertial space;
      (iii) rail means supporting said translation stages permitting movement of said platform along said three orthogonal axes;
      (iv) drive means for moving said translation stages along said rail means; and
      (v) first control means for determining the position of and controlling movement of said translation stages along said rail means; and
   (c) a fine stage isolation mount carried by said platform means of the coarse stage isolation mount for supporting said gradiometer and adapted to attenuate second, high frequency displacements of the gradiometer relative to an aircraft and consequently relative to a flight path ideal to the measurement of gravity gradients, said second displacements being smaller than said first displacements.

2. The gravity gradient measuring system of claim 1 wherein said coarse stage isolation mount includes:
   a first frame for fixedly mounting the coarse stage isolation mount on a floor of an aircraft;
   first rails mounted on said first frame for extending parallel to a floor of an aircraft and defining one of said orthogonal axes;
   a second frame movably mounted on first rails for movement along said one of said orthogonal axes;
   second rails mounted on said second frame for extending parallel to a floor of an aircraft and perpendicular to said first rails and defining a second of said orthogonal axes;
   a third frame movably mounted on said second rails for movement along said second orthogonal axis; and
   third rails mounted on said third frame extending vertically with respect to an aircraft floor and hence perpendicular to said first rails end said second rails and defining a third of said orthogonal axes, said third rails movably supporting said platform means for movement along said third orthogonal axis.

3. The system of claim 1, wherein said first control means determines and controls the position of said fine stage isolation mount relative to an aircraft.

4. The system of claim 3, including an aircraft, wherein said coarse stage isolation mount is mounted in said aircraft and wherein said aircraft includes a navigation system and a flight control system, said flight control system and said navigation system interacting to control a flight path of said aircraft, said flight control system operable by a human pilot or an autopilot system.

5. The system of claim 4, wherein said fine stage isolation mount includes second control means for determining and controlling the position of said gravity gradiometer in the six degrees of freedom associated with motion of a rigid body.

6. The system of claim 5, wherein said second control means of said fine stage isolation mount directs said gravity gradiometer towards a home position measured relative to the aircraft, whereby induced accelerations on the gravity gradiometer are minimized.

7. The system of claim 1, wherein said fine stage isolation mount includes:
   a base mounted on said platform means of said coarse stage isolation mount;
   a floater magnetically levitated relative to said base, said floater supporting said gravity gradiometer;
   a plurality of accelerometers adapted to measure accelerations of said floater; and
   a plurality of position sensors adapted to measure a relative position of said floater with respect to said base in the six degrees of freedom associated with motion of a rigid body.

8. The system of claim 7, wherein said accelerometers are linear accelerometers or rotational accelerometers.

9. A method for obtaining fine resolution gravity gradient data comprising:
   transporting a gravity gradiometer on a fine stage isolation mount carried by a platform of a coarse stage isolation mount in an aircraft experiencing low and high frequency accelerations and displacements from a flight path ideal to the measurement of gravity gradient;
   isolating, in a coarse stage, the gradiometer from said low frequency accelerations and corresponding first displacements of the aircraft by sliding said platform and said fine stage isolation mount along three orthogonal axes relative to the aircraft in response to such first displacements of the aircraft relative to said ideal flight path;
   isolating, in a fine stage, the gradiometer from said high frequency accelerations and corresponding displacements by moving the gravity gradiometer on said fine stage isolation mount in response to second, high frequency displacements of the coarse stage platform relative to the aircraft said second displacements being smaller than said first displacements;
   tracking a position of said aircraft in the six degrees of freedom associated with motion of a rigid body;
   during said isolating of the gravity gradiometer from said accelerations and displacements by said coarse and fine stages, measuring gravity gradients using a gravity gradiometer; and
   tabulating said gravity gradients as a function of said position of said aircraft.

10. The method of claim 9, wherein said tracking comprises:
    identifying said position of said aircraft using an inertial navigation system or a global positioning system.

11. The method of claim 10, wherein isolating of said accelerations and displacements in said coarse stage comprises:

measuring accelerations of said coarse stage, measuring the position of said coarse stage relative to the aircraft; and counteracting said accelerations and displacements measured through application of counteracting force to the coarse stage to move said platform and the fine stage isolation mount along one or more of said orthogonal axes.

12. The method of claim 11, wherein isolating said accelerations and displacements in said fine stage comprises:

measuring accelerations of a floater carrying said gravity gradiometer and magnetically levitated relative to a base of said fine stage using electromagnets;

measuring the position of said floater relative to said base; and compensating for said accelerations through variable application of current through said electromagnets.

13. The method of claim 10, wherein isolating of said accelerations and displacements in said fine stage includes:

determining said position of said floater relative to said base;

applying forces to said fine stage responsive to said position determined so as to reposition said floater towards a home position in, and relative to said base over a long time period, whereby minimum accelerations are induced on the gravity gradiometer carried by said floater.

14. The method of claim 9, wherein said coarse stage isolates the gradiometer from accelerations having frequencies up to 1 Hz, and said fine stage isolates the gradiometer from accelerations above 1 Hz.

* * * * *